United States Patent
Scanlan et al.

(10) Patent No.: US 11,325,886 B2
(45) Date of Patent: May 10, 2022

(54) AMIDE COMPOUNDS, PHARMACEUTICAL COMPOSITIONS THEREOF, AND METHODS OF USING THE SAME

(71) Applicant: OREGON HEALTH & SCIENCE UNIVERSITY, Portland, OR (US)

(72) Inventors: Thomas S. Scanlan, Portland, OR (US); James Matthew Meinig, Portland, OR (US); Skylar J. Ferrara, Portland, OR (US); Tapasree Banerji, Portland, OR (US); Tania Banerji, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 622 days.

(21) Appl. No.: 16/325,096

(22) PCT Filed: Aug. 14, 2017

(86) PCT No.: PCT/US2017/046807
§ 371 (c)(1),
(2) Date: Feb. 12, 2019

(87) PCT Pub. No.: WO2018/032012
PCT Pub. Date: Feb. 15, 2018

(65) Prior Publication Data
US 2021/0284599 A1    Sep. 16, 2021

Related U.S. Application Data

(60) Provisional application No. 62/374,657, filed on Aug. 12, 2016.

(51) Int. Cl.
*C07C 235/08* (2006.01)
*C07C 235/06* (2006.01)
(Continued)

(52) U.S. Cl.
CPC .......... *C07C 235/08* (2013.01); *C07C 235/06* (2013.01); *C07C 235/10* (2013.01);
(Continued)

(58) Field of Classification Search
None
See application file for complete search history.

(56) References Cited

U.S. PATENT DOCUMENTS

| | | | | |
|---|---|---|---|---|
| 5,466,569 | A | * 11/1995 | Weber | ................ G03C 7/39216 430/372 |
| 5,883,294 | A | 3/1999 | Scanlan et al. | |

(Continued)

FOREIGN PATENT DOCUMENTS

| CN | 1186332 C | 1/2005 |
|---|---|---|
| CN | 101180097 A | 5/2008 |

(Continued)

OTHER PUBLICATIONS

AU2017310535, "First Examination Report", dated Nov. 20, 2020, 4 pages.

(Continued)

*Primary Examiner* — Sudhakar Katakam
*Assistant Examiner* — Jennifer C Sawyer
(74) *Attorney, Agent, or Firm* — Kilpatrick Townsend & Stockton LLP

(57) ABSTRACT

Amide compounds are disclosed. Also disclosed are pharmaceutical compositions comprising the compounds as well as methods of treating neurodegenerative diseases that involve administering the compounds or pharmaceutical compositions to a subject.

14 Claims, 2 Drawing Sheets

(51) Int. Cl.
| | |
|---|---|
| *C07C 235/10* | (2006.01) |
| *C07C 235/16* | (2006.01) |
| *C07C 243/14* | (2006.01) |
| *C07C 255/29* | (2006.01) |
| *C07C 259/06* | (2006.01) |
| *C07C 309/15* | (2006.01) |
| *C07C 311/05* | (2006.01) |
| *C07D 305/08* | (2006.01) |

(52) U.S. Cl.
CPC .......... *C07C 235/16* (2013.01); *C07C 243/14* (2013.01); *C07C 255/29* (2013.01); *C07C 259/06* (2013.01); *C07C 309/15* (2013.01); *C07C 311/05* (2013.01); *C07D 305/08* (2013.01)

(56) References Cited

U.S. PATENT DOCUMENTS

| | | |
|---|---|---|
| 7,288,571 B2 | 10/2007 | Hangeland et al. |
| 10,226,438 B2 | 3/2019 | Scanlan et al. |
| 2005/0282872 A1 | 12/2005 | Hangeland et al. |
| 2009/0028925 A1 | 1/2009 | Erion et al. |
| 2009/0318514 A1 | 12/2009 | Garcia Collazo et al. |

FOREIGN PATENT DOCUMENTS

| | | | |
|---|---|---|---|
| CN | 105431163 | A | 3/2016 |
| JP | 2004512303 | A | 4/2004 |
| JP | 2004517037 | A | 6/2004 |
| JP | 2008542301 | A | 11/2008 |
| JP | 2008545711 | A | 12/2008 |
| JP | 2016517884 | A | 6/2016 |
| RU | 2007148927 | A | 7/2009 |
| WO | 0039077 | A2 | 7/2000 |
| WO | 2006128056 | A2 | 11/2006 |

OTHER PUBLICATIONS

EP17840413.3, "Extended European Search Report", dated Jan. 3, 2020, 9 pages.
Placzek et al., "New Synthetic Routes to Thyroid Hormone Analogs: D6-Sobetirome, 3H-Sobetirome, and the Antagonist Nh-3", Tetrahedron, vol. 71, No. 35, May 20, 2015, pp. 5946-5951.
Zaman et al., "Synthesis, Characterization And In Vitro Hydrolysis Studies Of Ester And Amide Prodrugs Of Dexibuprofen", Medicinal Chemistry Research, Birkhauser-verlag, Boston, vol. 21, No. 11, Nov. 17, 2011, pp. 3361-3368.
MX/A/2019/001634, "Office Action", dated Oct. 7, 2021, 6 pages.
RU2019106656, "Notice of Decision to Grant", dated Oct. 1, 2021, 32 pages.
PCT/US2017/046807, "International Preliminary Report on Patentability", dated Feb. 21, 2019, 9 pages.
CN201780063087.9, "Office Action", dated Apr. 2, 2021, 10 pages.
IL264765, "Office Action", dated Jan. 14, 2021, 7 pages.
IN201917006950, "First Examination Report", dated May 29, 2021, 7 pages.
Ferrara et al., "Ester-to-amide Rearrangement Of Ethanolamine-derived Prodrugs of Sobetirome With Increased Blood-brain Barrier Penetration", Bioorganic & Medicinal Chemistry; vol. 25, Issue 10, May 15, 2017, pp. 2743-2753.
Meinig et al., "Targeting Fatty-Acid Amide Hydrolase with Prodrugs for CNS-Selective therapy", ACS Chemical Neuroscience; available online at:—http://pubs.acs.org/doi/pdf/1 0.1 021/acschemneuro. 7b00239, Jul. 30, 2017.
PCT/US2017/046807, "PCT Search Report", dated Oct. 19, 2017, 12 pages.
IL264765, "Office Action", dated Jan. 7, 2021, 7 pages.
RU2019106656, "Office Action", dated Jan. 12, 2021, 18 pages.
JP2019-507271, "Office Action", dated Jul. 12, 2021, 8 pages.
Larsen et al., "Textbook of Drug Desining and Discovery", Third Edition, 2005.
MX/A/2019/001634, "Office Action", dated Apr. 19, 2021, 7 pages.
Tegeli et al., "Synthesis and evaluation of amide prodrugs of mefenamic acid, International Journal of Chemical Sciences", vol. 12, No. 3, 2014, pp. 1033-1043.
AU2017310535, "Notice of Acceptance", dated Nov. 2, 2021, 3 pages.
EP17840413.3, "Office Action", dated Sep. 15, 2020, 3 pages.
BR112019002799-8, "Office Action", dated Jan. 4, 2022, 8 pages.
JP2019-507271, "Office Action" with Machine translation, dated Feb. 7, 2022, 6 pages.
CN201780063087.9, "Office Action", dated Jan. 6, 2022, 14 pages.
Ferrara et al., "Ester-to-Amide Rearrangement of Ethanolamine-Derived Prodrugs of Sobetirome with Increased Blood-Brain Barrier Penetration", Bioorganic & Medicinal Chemistry, vol. 25, No. 10, Mar. 23, 2017, pp. 2743-2753.

\* cited by examiner

AMIDE COMPOUNDS, PHARMACEUTICAL COMPOSITIONS THEREOF, AND METHODS OF USING THE SAME

RELATED APPLICATIONS

This application claims priority to U.S. provisional patent application No. 62/374,657, filed Aug. 12, 2017.

This application is related to U.S. 62/119,001, filed 20 Feb. 2015; PCT/US16/18732, filed 19 Feb. 2016; U.S. Ser. No. 15/048,672, filed 19 Feb. 2016; U.S. 62/338,178 filed 18 May 2016; U.S. 61/819,467, filed 3 May 2013; PCT/US13/53640, filed 5 Aug. 2013; PCT/US14/14943, filed 5 Feb. 2014; and U.S. Ser. No. 14/888,577, filed 2 Nov. 2015. All of the above applications are incorporated by reference herein.

FIELD

Generally, the field is medicinal compounds and pharmaceutical compositions. More specifically, the invention relates to medicinal amide compounds. The amide compounds may exhibit improved transit to the central nervous system.

BACKGROUND

There is increasing interest in activating specific thyroid hormone signaling pathways in the brain for the treatment of certain CNS diseases, in particular those that involve myelination defects (Fourcade S et al, *Mol Pharmacol* 63, 1296-1303 (2003) and Baxi E G et al, *Glia* 62, 1513-1529 (2014); both of which are incorporated by reference herein). Thyroid hormones T4 and T3 are not suitable as therapeutics for these indications as there is no therapeutic index for T4 and T3 separating the desired therapeutic effect from adverse effects associated with hyperthyroidism such as tachycardia, muscle wasting, and osteoporosis (Yen P M et al, *Physiol Rev* 81, 1097-1142 (2001); Yen P M et al, *Mol Cell Endocrinol* 246, 121-127 (2006); Biondi B and Klein I, *Endocrine* 24, 1-13 (2004); and Klein I and Ojamaa K, *Endocrinol Metab Clin North Am* 27, 51-62 (1998); all of which are incorporated by reference herein). This issue may be potentially addressed by certain synthetic T3 agonists that show tissue selective thyroid hormone action (Joharapurkar A A et al, *J Med Chem* 55, 5649-5675 (2012); incorporated by reference herein.)

Sobetirome (also known as GC-1) is an example that has been studied extensively over the past 15 years (Scanlan T S, *Heart Fail Rev* 15, 177-182 (2010); incorporated by reference herein). It is believed that sobetirome and T3 affect LDL cholesterol lowering by stimulating hepatic cholesterol clearance mechanisms. Advantageously, sobetirome produces this effect substantially without deleterious effect on heart, muscle, or bone (Grover G J et al, *Endocrinology* 145, 1656-1661 (2004); incorporated by reference herein). The use of sobetirome for the treatment of neurodegenerative diseases was previously disclosed (WO 2014/178931). Improvements in the efficiency of the distribution to the CNS are often desirable for therapeutic agents targeting neurodegenerative diseases. There is a need for compounds having improved CNS distribution for the treatment of neurodegenerative diseases (e.g., demyelinating diseases).

SUMMARY OF THE INVENTION

In one aspect, the invention features a compound of Formula I:

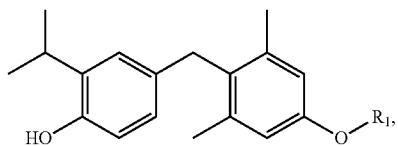

Formula I or a pharmaceutically acceptable salt thereof, wherein $R_1$ is an amide.

In some embodiments of this aspect, the compound is of Formula II:

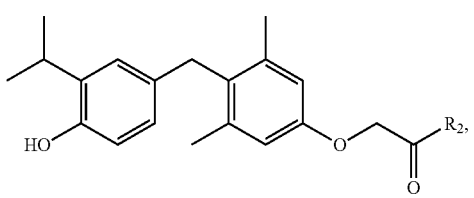

Formula II or a pharmaceutically acceptable salt thereof, wherein $R_2$ is alkylamino.

In some embodiments of this aspect, the compound is of Formula II:

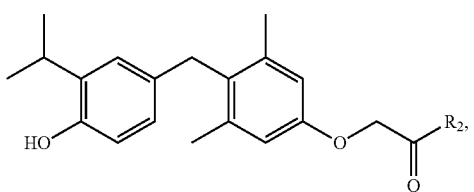

Formula II or a pharmaceutically acceptable salt thereof, wherein $R_2$ is amino.

In some embodiments, the compound is of Formula III:

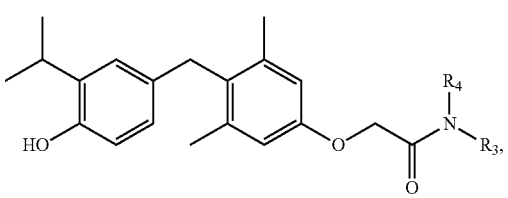

Formula III or a pharmaceutically acceptable salt thereof, wherein each of $R_3$ and $R_4$ is, independently, H, alkyl, cycloalkyl, substituted alkyl, unsubstituted alkyl, heteroalkyl, saturated alkyl, unsaturated alkyl, aryl, amino, or ethoxy. In some particular embodiments, $R_3$ is methyl and $R_4$ is methyl.

In some embodiments, the compound is of Formula IV:

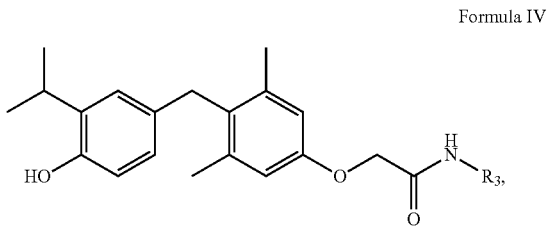

Formula IV or a pharmaceutically acceptable salt thereof, wherein $R_3$ is H, hydroxyl, amino, methyl, ethyl, propyl, cyclopropyl, 2-hydroxyethyl, 1-hydroxypropan-2-yl, 2-hydroxypropyl, 2-aminoethyl acetate, 2-fluoroethyl, 2,2-difluoroethyl, 2,2,2-trifluoroethyl, phenyl, (4-nitro)phenyl, 2-phenylethyl 2-(2-hydroxyphenyl)ethyl, 2-(3-hydroxyphenyl)ethyl, 2-(3,4-dihydroxyphenyl)ethyl, 3-fluoroethyl; S-methylsulfonyl, 1-(2-hydroxyethyl)-2-hydroxyethyl, 2-propenyl, 2-propynyl, methoxy, 2-ethylsulfonate sodium, cyanomethyl, or oxetanyl.

In some embodiments, the compound is of Formula III:

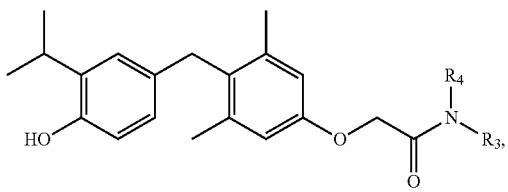

Formula III or a pharmaceutically acceptable salt thereof, wherein $R_4$ is selected from H and $C_{1-6}$ alkyl; and $R_3$ is: (a) H, OH, $NH_2$, —$NH(C_{1-6}$ alkyl), —$N(C_{1-6}$ alkyl$)_2$, —$SO_2H$, —$SO_2(C_{1-6}$ alkyl), $C_{2-6}$ alkenyl, $C_{2-6}$ alkynyl, $C_{3-6}$ cycloalkyl, or a 3- to 6-membered heterocyclyl ring containing one heteroatom selected from O, N, and S; or (b) $C_{1-6}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (c) —O—$C_{1-6}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (d) a phenyl group optionally substituted by 1, 2, or 3 substituents each independently selected from the group consisting of OH, $NO_2$, and halogen.

In some embodiments, the compound is of Formula IV:

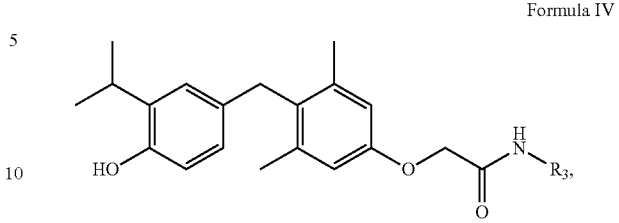

Formula IV or a pharmaceutically acceptable salt thereof, wherein $R_3$ is: (a) H, OH, $NH_2$, —$NH(C_{1-6}$ alkyl), —$N(C_{1-6}$ alkyl$)_2$, —$SO_2H$, —$SO_2(C_1$-6 alkyl), $C_{2-6}$ alkenyl, $C_{2-6}$ alkynyl, $C_{3-6}$ cycloalkyl, or a 3- to 6-membered heterocyclyl ring containing one heteroatom selected from O, N, and S; or (b) $C_{1-6}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (c) —O—$C_{1-6}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (d) a phenyl group optionally substituted by 1, 2, or 3 substituents each independently selected from the group consisting of OH, $NO_2$, and halogen.

In particular embodiments of a compound of Formula IV, $R_3$ is: (a) H, OH, $NH_2$, —$SO_2H$, —$SO_2(C_{1-3}$ alkyl), $C_{2-3}$ alkenyl, $C_{2-3}$ alkynyl, $C_{3-6}$ cycloalkyl, a 3- to 6-membered heterocyclyl ring containing one heteroatom selected from O, N, and S; or (b) $C_{1-4}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-3}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (c) —O—$C_{1-4}$ alkyl optionally substituted by 1, 2, or 3 substituents each independently selected from OH, halogen, $NH_2$, —$NH(C_{1-6}$ alkyl), —$N(C_{1-6}$ alkyl$)_2$, —$SO_2H$, —$SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; and (d) a phenyl group optionally substituted by 1, 2, or 3 substituents each independently selected from the group consisting of OH, $NO_2$, and halogen.

In particular embodiments of a compound of Formula IV, $R_3$ is: (a) H, OH, $NH_2$, —$SO_2H$, —$SO_2(CH_3)$, $C_{2-3}$ alkenyl, $C_{2-3}$ alkynyl, $C_{3-6}$ cycloalkyl, a 3- to 6-membered heterocyclyl ring containing one oxygen heteroatom; or (b) $C_{1-4}$ alkyl optionally substituted by 1, 2, or 3 substituents each independently selected from OH, F, $NH_2$, —$SO_2H$, —$SO_2(CH_3)$, CN, $C_{3-6}$ cycloalkyl, a 3- to 6-membered heterocyclyl ring containing one oxygen heteroatom, or a phenyl group optionally substituted by 1, 2, or 3 substituents each independently selected from the group consisting of OH, $NO_2$, and F; or (c) —O—$C_{1-4}$ alkyl optionally substituted by 1, 2, or 3 substituents each independently selected from OH, F, $NH_2$, —$SO_2H$, —$SO_2(CH_3)$, CN, $C_{3-6}$ cycloalkyl, a 3- to 6-membered heterocyclyl ring containing one oxygen heteroatom, or a phenyl group optionally substituted by 1, 2, or 3 substituents each independently selected from the group consisting of OH, $NO_2$, and F; or (d) a phenyl group optionally substituted by 1, 2, or 3 substituents each independently selected from the group consisting of OH, $NO_2$, and F.

In some embodiments, the compound is of Formula IV:

Formula IV

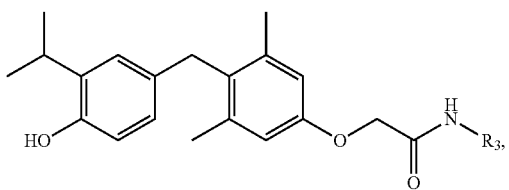

or a pharmaceutically acceptable salt thereof, wherein $R_3$ is —$(CH_2)n^1$-phenyl, and wherein $n^1$ is an integer selected from 0, 1, 2, 3, or 4, and the phenyl ring is optionally substituted by 1, 2, or 3 substituents each independently selected from the group consisting of OH, $NO_2$, and halogen.

In some embodiments, the compound is of Formula IV:

Formula IV

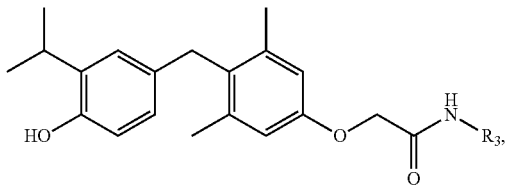

or a pharmaceutically acceptable salt thereof, wherein $R_3$ is —$(CH_2)n^2$-phenyl, wherein $n^2$ is an integer selected from 0, 1, or 2, and the phenyl ring is optionally substituted by 1, 2, or 3 substituents each independently selected from the group consisting of OH, $NO_2$, and halogen.

In some embodiments, the compound is of Formula IV:

Formula IV

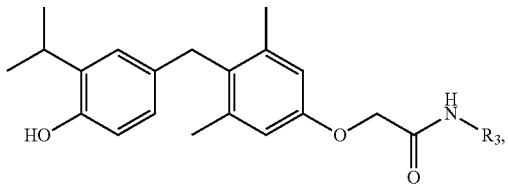

or a pharmaceutically acceptable salt thereof, wherein $R_3$ is —$(CH_2)n^2$-phenyl, wherein $n^2$ is an integer selected from 0, 1, or 2, and the phenyl ring is optionally substituted by 1, 2, or 3 substituents each independently selected from the group consisting of OH, $NO_2$, and F.

In some embodiments, the compound is of Formula IV:

Formula IV

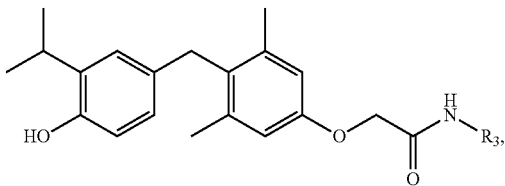

or a pharmaceutically acceptable salt thereof, wherein $R_3$ is —$(CH_2)$-phenyl, wherein the phenyl ring is optionally substituted by 1, 2, or 3 substituents each independently selected from the group consisting of OH, $NO_2$, and F.

In some embodiments, the compound is of Formula IV:

Formula IV

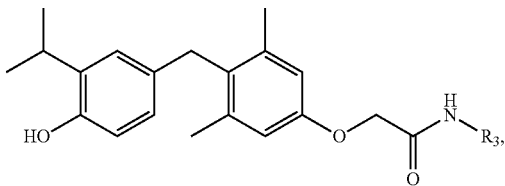

or a pharmaceutically acceptable salt thereof, wherein $R_3$ is $C_{1-6}$ alkyl optionally substituted by 1, 2, or 3 substituents each independently selected from the group consisting of OH, F, $NH_2$, —$SO_2H$, —$SO_2(CH_3)$, CN, $C_{3-6}$ cycloalkyl, and a 3- to 6-membered heterocyclyl ring containing one oxygen heteroatom.

In some embodiments, the compound is of Formula IV:

Formula IV

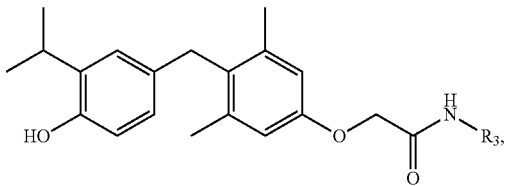

or a pharmaceutically acceptable salt thereof, wherein $R_3$ is $C_{1-4}$ alkyl optionally substituted by 1, 2, or 3 substituents each independently selected from the group consisting of OH, F, $NH_2$, —$SO_2H$, —$SO_2(CH_3)$, CN, $C_{3-6}$ cycloalkyl, and a 3- to 6-membered heterocyclyl ring containing one oxygen heteroatom.

In some embodiments, the compound is of Formula IV:

Formula IV

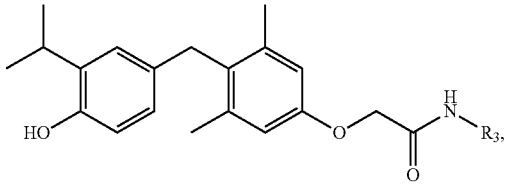

or a pharmaceutically acceptable salt thereof, wherein $R_3$ is $C_{1-6}$ alkyl optionally substituted by 1, 2, or 3 substituents each independently selected from the group consisting of OH, F, $NH_2$, CN, —$SO_2H$, and —$SO_2(C_{1-6}$ alkyl).

In some embodiments, the compound is of Formula IV:

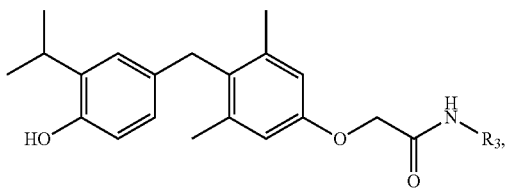

Formula IV or a pharmaceutically acceptable salt thereof, wherein $R_3$ is $C_{1-6}$ alkyl optionally substituted by 1, 2, or 3 OH substituents.

In some embodiments, the compound is of Formula IV:

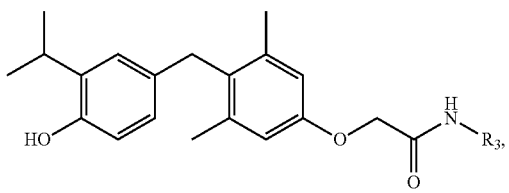

Formula IV or a pharmaceutically acceptable salt thereof, wherein $R_3$ is $C_{1-4}$ alkyl optionally substituted by 1, 2, or 3 OH substituents.

In some embodiments, the compound is of Formula IV:

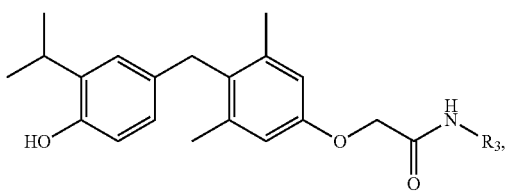

Formula IV or a pharmaceutically acceptable salt thereof, wherein $R_3$ is $C_{1-6}$ alkyl optionally substituted by 1, 2, or 3 F substituents.

In some embodiments, the compound is of Formula IV:

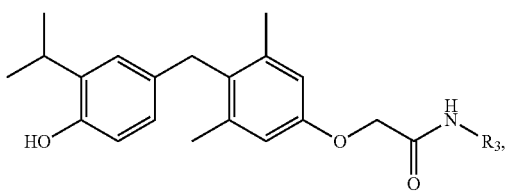

Formula IV or a pharmaceutically acceptable salt thereof, wherein $R_3$ is $C_{1-4}$ alkyl optionally substituted by 1, 2, or 3 F substituents.

In some embodiments, the compound is of Formula IV:

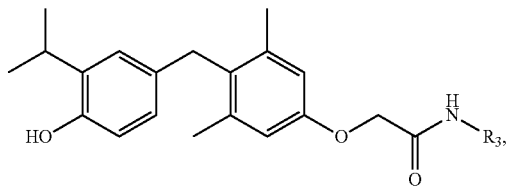

Formula IV or a pharmaceutically acceptable salt thereof, wherein $R_3$ is —O—$C_{1-6}$ alkyl optionally substituted by 1, 2, or 3 F substituents.

In some embodiments, the compound is of Formula IV:

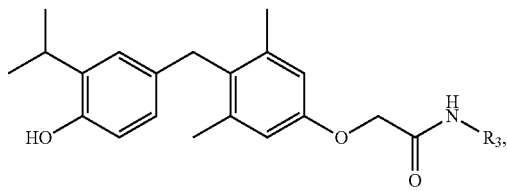

Formula IV or a pharmaceutically acceptable salt thereof, wherein $R_3$ is —O—$C_{1-4}$ alkyl optionally substituted by 1, 2, or 3 F substituents.

In some embodiments, the compound is of Formula IV:

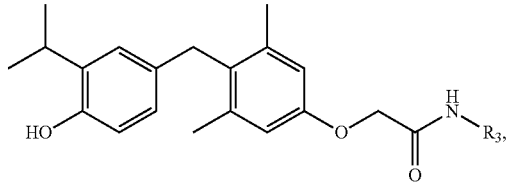

Formula IV or a pharmaceutically acceptable salt thereof, wherein $R_3$ is —O—$C_{1-6}$ alkyl.

In some embodiments, the compound is of Formula IV:

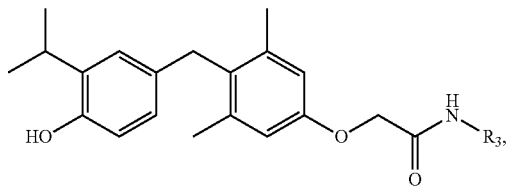

Formula IV or a pharmaceutically acceptable salt thereof, wherein $R_3$ is —O—$C_{1-4}$ alkyl.

In some embodiments, the compound is of Formula III:

Formula III

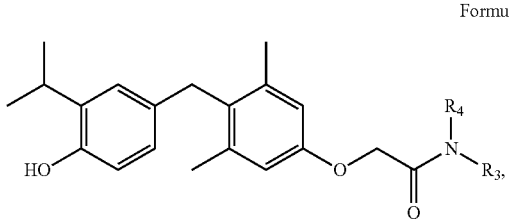

or a pharmaceutically acceptable salt thereof, wherein each of $R_3$ and $R_4$ is, independently, H, substituted aliphatic, unsubstituted aliphatic, substituted phenyl, unsubstituted phenyl, $OR^{N1}$, $-N(R^{N1})_2$, or $-SO_2(R^{N2})$ wherein each $R^{N1}$ is independently H, substituted aliphatic, or unsubstituted aliphatic, and $R^{N2}$ is OH, unsubstituted aliphatic, or substituted aliphatic; provided that, if one $R^N$ is $OR^{N1}$, $-N(R^{N1})_2$, or $-SO_2(R^{N2})$, the other $R^N$ is H, substituted aliphatic, unsubstituted aliphatic, substituted phenyl, or unsubstituted phenyl. In particular embodiments, $R_3$ is H or unsubstituted aliphatic. In particular embodiments, $R_4$ is H, substituted aliphatic, or unsubstituted aliphatic. In particular embodiments, $R_3$ is methyl. In particular embodiments, $R_4$ is methyl.

In another aspect, the invention features a compound selected from the group consisting of:

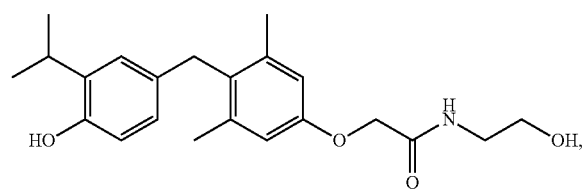

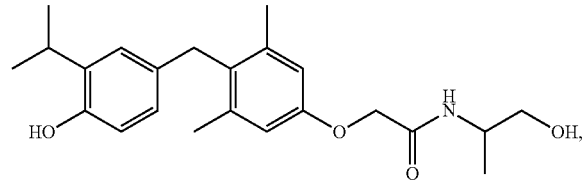

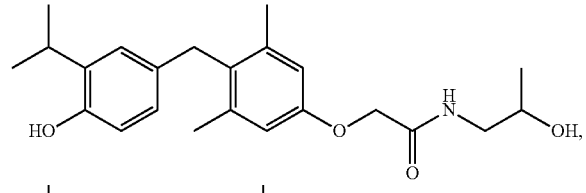

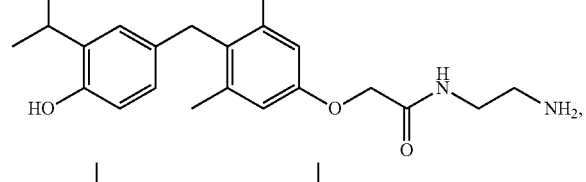

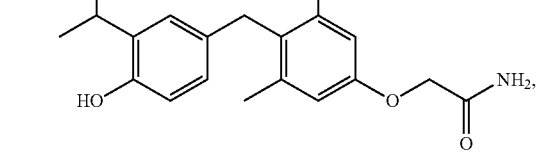

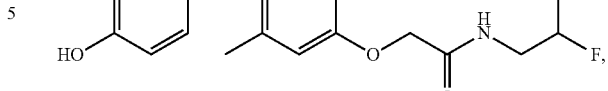

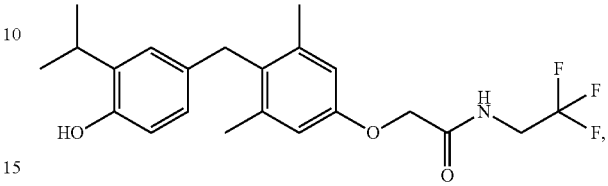

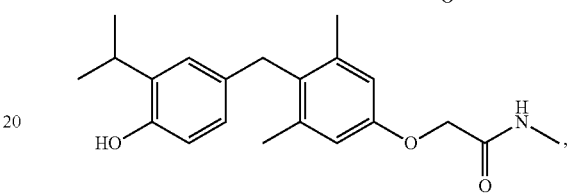

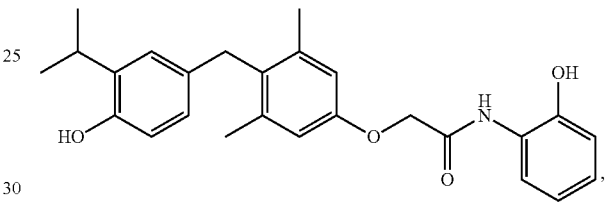

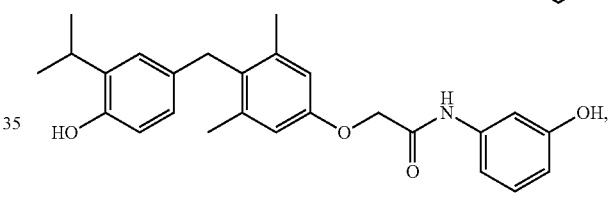

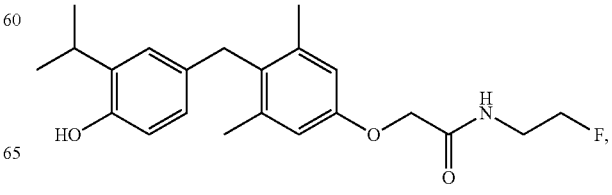

11

-continued

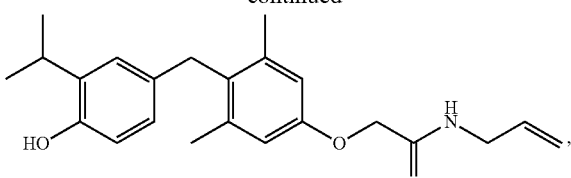

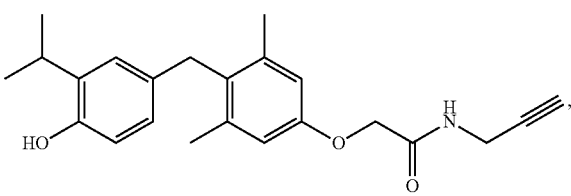

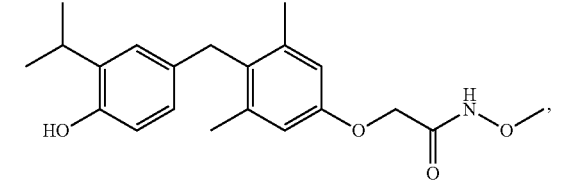

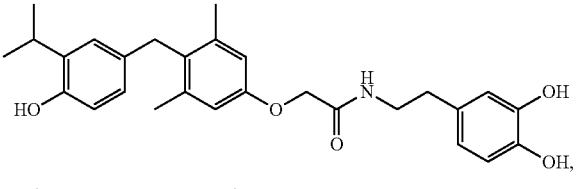

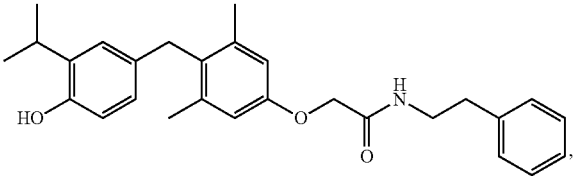

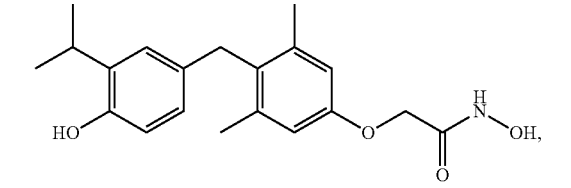

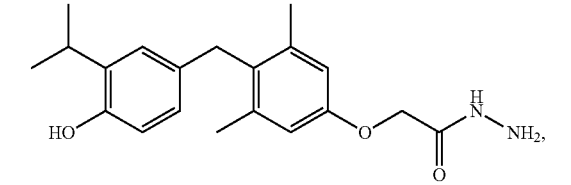

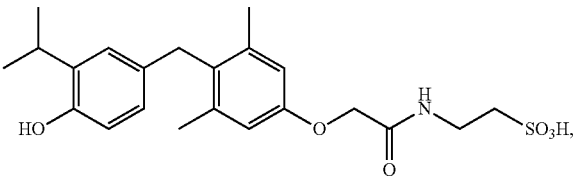

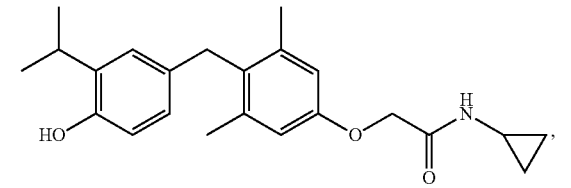

12

-continued

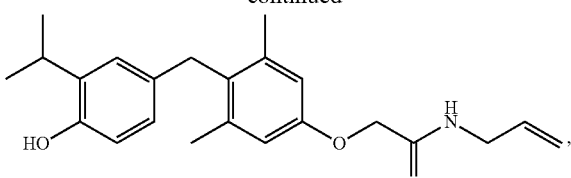

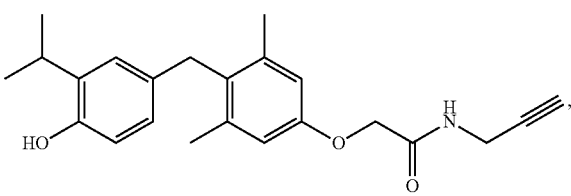

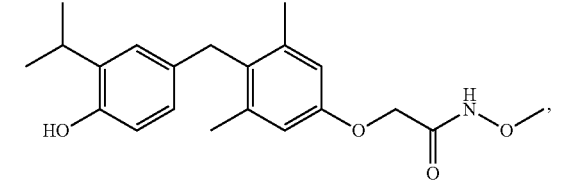

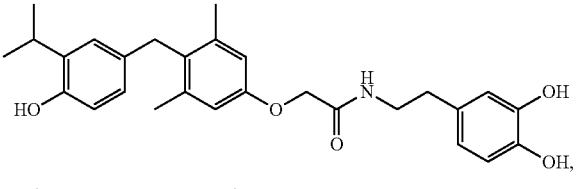

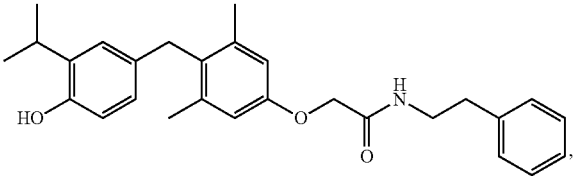

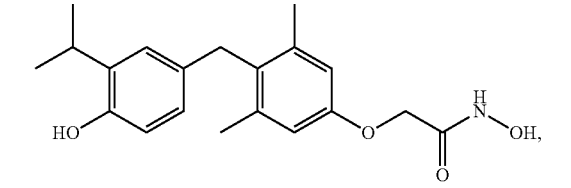

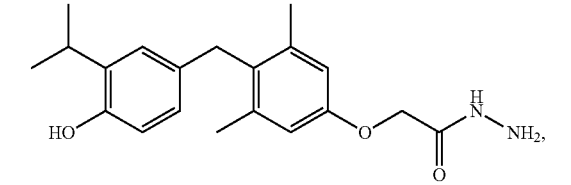

or a pharmaceutically acceptable salt thereof.

In some embodiments of the first aspect of the invention, the compound is selected from the group consisting of:
2-(4-(4-hydroxy-3-isopropylbenzyl)-3,5-dimethylphenoxy)-N-(2-hydroxyethyl)acetamide;
2-(4-(4-hydroxy-3-isopropylbenzyl)-3,5-dimethylphenoxy)-N-(1-hydroxypropan-2-yl)acetamide;
2-(4-(4-hydroxy-3-isopropylbenzyl)-3,5-dimethylphenoxy)-N-(2-hydroxypropyl)acetamide;
2-(2-(4-(4-hydroxy-3-isopropylbenzyl)-3,5-dimethylphenoxy)acetamido)ethan-1-aminium acetate;
2-(4-(4-hydroxy-3-isopropylbenzyl)-3,5-dimethylphenoxy)acetamide;
N-(2,2-difluoroethyl)-2-(4-(4-hydroxy-3-isopropylbenzyl)-3,5-dimethylphenoxy)acetamide;
2-(4-(4-hydroxy-3-isopropylbenzyl)-3,5-dimethylphenoxy)-N-(2,2,2-trifluoroethyl)acetamide;
2-(4-(4-hydroxy-3-isopropylbenzyl)-3,5-dimethylphenoxy)-N-methylacetamide;
2-(4-(4-hydroxy-3-isopropyl benzyl)-3,5-dimethylphenoxyl)-N-(2-hydroxyphenyl) acetamide;
2-(4-(4-hydroxy-3-isopropyl benzyl)-N-(3-hydroxyphenyl) acetamide;

2-(4-(4-hydroxy-3-isopropylbenzyl)-3,5-dimethylphenoxy)-N-(2-(methylsulfonamido)ethyl)acetamide;
N-(1,3-dihydroxypropan-2-yl)-2-(4-(4-hydroxy-3-isopropylbenzyl)-3,5-dimethylphenoxy)acetamide
2-(4-(4-hydroxy-3-isopropylbenzyl)-3,5-dimethylphenoxy)-N-propylacetamide;
N-(2-fluoroethyl)-2-(4-(4-hydroxy-3-isopropylbenzyl)-3,5-dimethylphenoxy)acetamide;
N-allyl-2-(4-(4-hydroxy-3-isopropylbenzyl)-3,5-dimethylphenoxy)acetamide;
2-(4-(4-hydroxy-3-isopropylbenzyl)-3,5-dimethylphenoxy)-N-(prop-2-yn-1-yl)acetamide;
2-(4-(4-hydroxy-3-isopropylbenzyl)-3,5-dimethylphenoxy)-N-methoxyacetamide;
N-(3,4-dihydroxyphenethyl)-2-(4-(4-hydroxy-3-isopropylbenzyl)-3,5-dimethylphenoxy)acetamide;
2-(4-(4-hydroxy-3-isopropylbenzyl)-3,5-dimethylphenoxy)-N-phenethylacetamide;
N-hydroxy-2-(4-(4-hydroxy-3-isopropylbenzyl)-3,5-dimethylphenoxy)acetamide;
2-(4-(4-hydroxy-3-isopropylbenzyl)-3,5-dimethylphenoxy)acetohydrazide;
2-(2-(4-(4-hydroxy-3-isopropylbenzyl)-3,5-dimethylphenoxy)acetamido)ethane-1-sulfonate
N-cyclopropyl-2-(4-(4-hydroxy-3-isopropylbenzyl)-3,5-dimethylphenoxy)acetamide;
2-(4-(4-hydroxy-3-isopropylbenzyl)-3,5-dimethylphenoxy)-N,N-dimethylacetamide;
N-ethyl-2-(4-(4-hydroxy-3-isopropylbenzyl)-3,5-dimethylphenoxy)acetamide;
N-(cyanomethyl)-2-(4-(4-hydroxy-3-isopropylbenzyl)-3,5-dimethylphenoxy)acetamide;
N-(3-fluorophenyl)-2-(4-(4-hydroxy-3-isopropylbenzyl)-3,5-dimethylphenoxy)acetamide;
2-(4-(4-hydroxy-3-isopropylbenzyl)-3,5-dimethylphenoxy)-N-(oxetan-3-yl)acetamide; and
2-(4-(4-hydroxy-3-isopropylbenzyl)-3,5-dimethylphenoxy)-N-(4-nitrophenyl)acetamide; or a pharmaceutically acceptable salt thereof.

In another aspect, the invention features a pharmaceutical composition comprising a pharmaceutically effective amount of a compound described herein (e.g., a compound of any one of the previous aspects), or a pharmaceutically acceptable salt thereof, and one or more pharmaceutically acceptable carriers.

In another aspect, the invention features a method of treating a subject having a neurodegenerative disease by administering a pharmaceutically effective amount of a compound described herein (e.g., a compound of any one of the previous aspects), or a pharmaceutically acceptable salt thereof, or a pharmaceutical composition described herein, to the subject, thereby treating the neurodegenerative disease.

In some embodiments of this aspect, the neurodegenerative disease is a demyelinating disease. In some embodiments of this aspect, the neurodegenerative disease is X-linked adrenoleukodystrophy or multiple sclerosis.

In some embodiments of this aspect, the neurodegenerative disease is selected from the group consisting of acute disseminated encephalomyelitis, acute hemorrhagic leukoencephalitis, adult Refsum disease, Alexander disease, Alzheimer's disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barré syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, Multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, and Zellweger syndrome.

In another aspect, the invention features a method of treating a subject having Alzheimer's disease by administering a pharmaceutically effective amount of a compound described herein (e.g., a compound of any one of the previous aspects), or a pharmaceutically acceptable salt thereof, or a pharmaceutical composition described herein, to the subject, thereby treating the Alzheimer's disease.

In another aspect, the invention features a method of treating a subject having a disease or condition selected from the group consisting of Acute disseminated encephalomyelitis (ADEM), Acute hemorrhagic leukoencephalitis (AHL or AHLE), Adult Refsum disease, Infantile Refsum disease, Alexander disease, Alzheimer's disease, Balo concentric sclerosis, Canavan disease, Central pontine myelinolysis (CPM), Cerebral palsy, Cerebrotendineous xanthomatosis, Chronic inflammatory demyelinating polyneuropathy (CIDP), Devic's syndrome, Diffuse myelinoclastic sclerosis, Encephalomyelitis, Guillain-Barré syndrome, Idiopathic inflammatory demyelinating disease (IIDD), Krabbe disease, Leber hereditary optic neuropathy, Leukodystrophy, Marburg multiple sclerosis, Marchiafava-Bignami disease, Metachromatic leukodystrophy (MLD), Multifocal motor neuropathy (MMN), Multiple sclerosis (MS), Paraproteinemic demyelinating polyneuropathy, Pelizaeus-Merzbacher disease (PMD), Progressive multifocal leukoencephaalopathy (PML), Tropical spastic paraparesis (TSP), X-linked adrenoleukodystrophy (X-ALD, ALD, or X-linked ALD), and Zellweger by administering a pharmaceutically effective amount of a compound described herein (e.g., a compound of any one of the previous aspects), or a pharmaceutically acceptable salt thereof, or a pharmaceutical composition described herein, to the subject, thereby treating the disease or condition.

In another aspect, the invention features a compound described herein (e.g., a compound of any one of the previous aspects), or a pharmaceutically acceptable salt thereof, or a pharmaceutical composition described herein, for use in the treatment of a neurodegenerative disease (e.g., a demyelinating disease, X-linked adrenoleukodystrophy, or multiple sclerosis).

In some embodiments, the compound, or the pharmaceutically acceptable salt thereof, or the pharmaceutical composition, is for use in treating a neurodegenerative disease is selected from the group consisting of acute disseminated encephalomyelitis, acute hemorrhagic leukoencephalitis, adult Refsum disease, Alexander disease, Alzheimer's disease, balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barré syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, Multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, and Zellweger syndrome.

In another aspect, the invention features a compound described herein (e.g., a compound of any one of the previous aspects), or a pharmaceutically acceptable salt thereof, or a pharmaceutical composition described herein, for use in the treatment of Alzheimer's disease.

In another aspect, the invention features a compound described herein (e.g., a compound of any one of the previous aspects), or a pharmaceutically acceptable salt thereof, or a pharmaceutical composition described herein, for use in the treatment of a disease or condition selected from the group consisting of Acute disseminated encephalomyelitis (ADEM), Acute hemorrhagic leukoencephalitis (AHL or AHLE), Adult Refsum disease, Infantile Refsum disease, Alexander disease, Alzheimer's disease, Balo concentric sclerosis, Canavan disease, Central pontine myelinolysis (CPM), Cerebral palsy, Cerebrotendineous xanthomatosis, Chronic inflammatory demyelinating polyneuropathy (CIDP), Devic's syndrome, Diffuse myelinoclastic sclerosis, Encephalomyelitis, Guillain-Barré syndrome, Idiopathic inflammatory demyelinating disease (IIDD), Krabbe disease, Leber hereditary optic neuropathy, Leukodystrophy, Marburg multiple sclerosis, Marchiafava-Bignami disease, Metachromatic leukodystrophy (MLD), Multifocal motor neuropathy (MMN), Multiple sclerosis (MS), Paraproteinemic demyelinating polyneuropathy, Pelizaeus-Merzbacher disease (PMD), Progressive multifocal leukoencephaalopathy (PML), Tropical spastic paraparesis (TSP), X-linked adrenoleukodystrophy (X-ALD, ALD, or X-linked ALD), and Zellweger syndrome.

DETAILED DESCRIPTION OF THE INVENTION

Definitions

Figure 1:
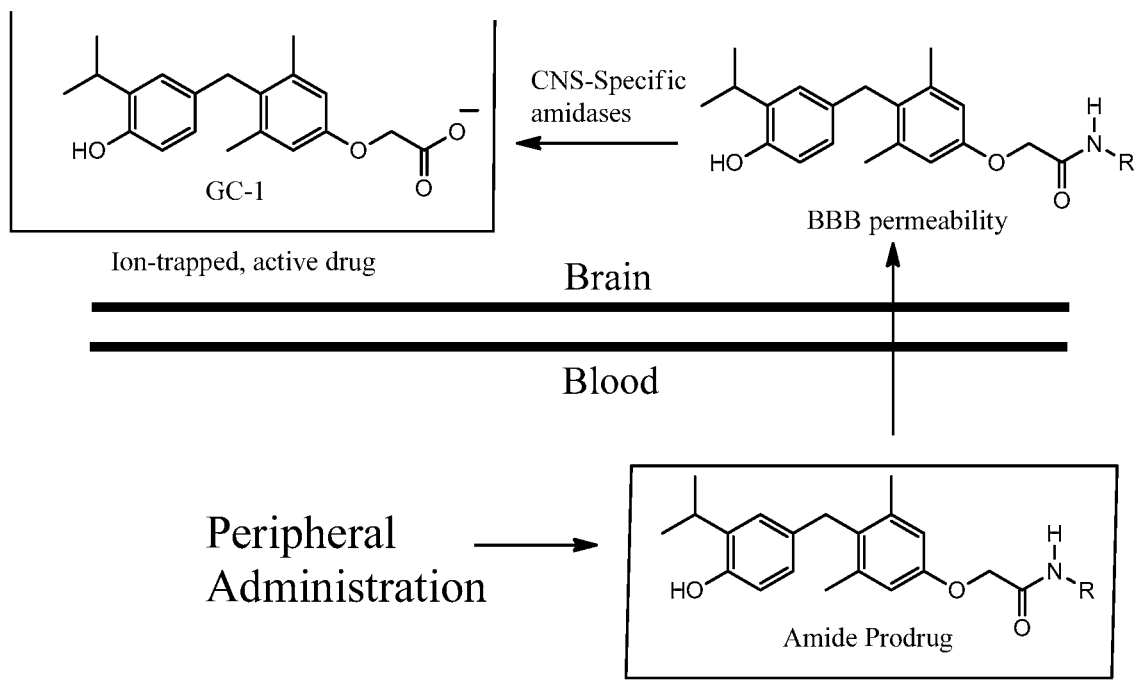
FIG. 1 is a general approach for CNS targeted compounds disclosed herein.
Figure 2A:
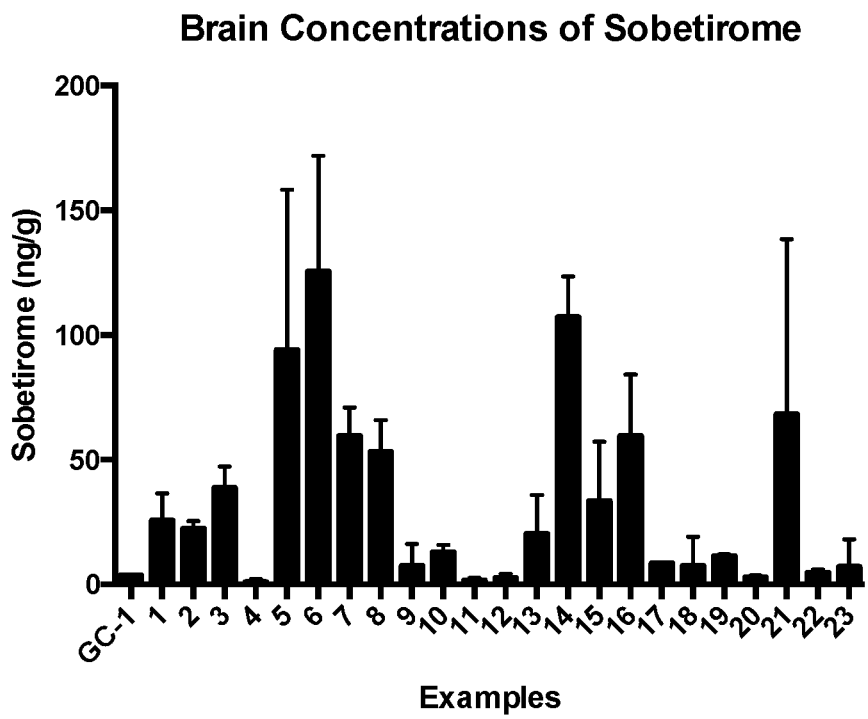
FIG. 2A is a graph of the brain concentrations of sobetirome (GC-1) or the disclosed compounds after intraperitoneal administration to mice.
Figure 2B:
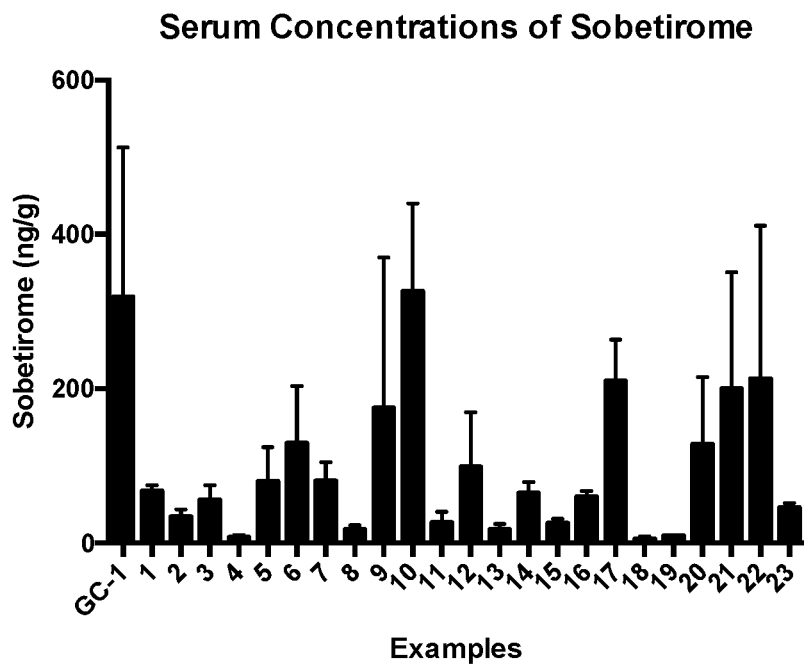
FIG. 2B is a graph of the serum concentrations of sobetirome (GC-1) or the disclosed compounds after intraperitoneal administration to mice.
Figure 2C:
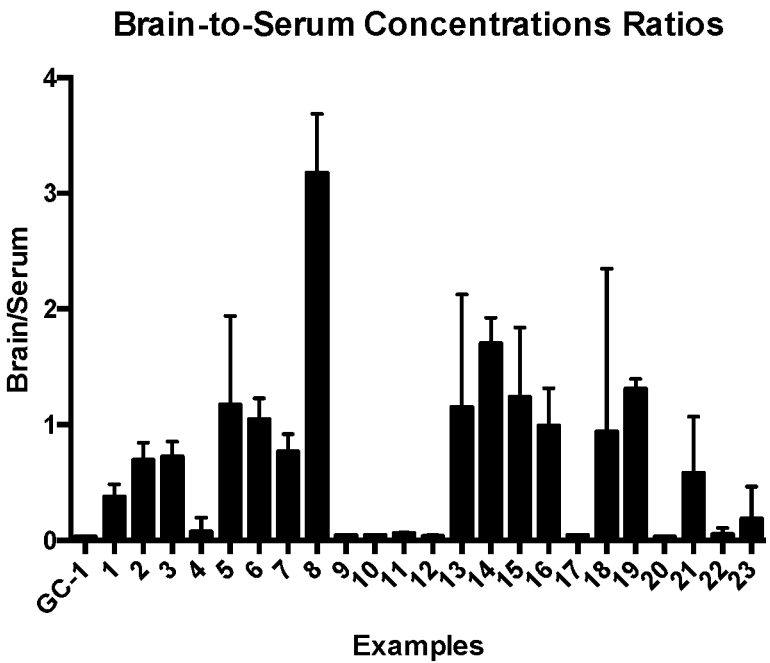
FIG. 2C is a graph of the ratio of brain concentration to serum concentration of sobetirome (GC-1) or the disclosed compounds after intraperitoneal administration to mice.

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as R, including all subvariables thereof (such as $R_1$, $R_2$, etc.) used throughout the disclosure are the same variables as previously defined unless stated to the contrary.

Administration: Refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

Aliphatic: a branched, linear, or cyclic non-aromatic hydrocarbon group of 1 to 6 carbon atoms. An aliphatic group is saturated or unsaturated. An unsaturated aliphatic group contains one carbon-carbon double or triple bond. A substituted aliphatic group is an aliphatic group substituted with 1 to 5 substituents, valency permitting. Each substituent in the substituted aliphatic group is independently selected from the group consisting of halogen, —$OR^A$, —$N(R^B)_2$, —$SO_2(R^C)$, cyano, substituted phenyl, and unsubstituted phenyl; where $R^A$ is H, unsubstituted aliphatic, unsubstituted phenyl, or substituted phenyl; each $R^B$ is independently unsubstituted aliphatic, unsubstituted phenyl, substituted phenyl, or $SO_2(R^C)$; and $R^C$ is independently —OH, unsubstituted aliphatic, or unsubstituted phenyl, substituted phenyl.

Alkyl: a branched or unbranched saturated hydrocarbon group, such as, without limitation, methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like. A lower alkyl group is a saturated branched or unbranched hydrocarbon having from 1 to 6 carbon atoms ($C_{1-6}$ alkyl). The term alkyl also encompasses cycloalkyls. An unsaturated alkyl may be an alkenyl (e.g., a group containing one or more carbon-carbon double bonds) or an alkynyl (e.g., a group containing one or more carbon-carbon triple bonds). Alkyl also encompasses substituted alkyls which are alkyl groups wherein one or more hydrogen atoms are replaced with a substituent such as, without limitation, alkyl, alkynyl, alkenyl, aryl, halide, nitro, amino, ester, ether, ketone, aldehyde, hydroxyl, carboxyl, cyano, amido, haloalkyl, haloalkoxy, or alkoxy. The term alkyl also encompasses heteroalkyls. A heteroalkyl contains at least one heteroatom such as nitrogen, oxygen, sulfur, or phosphorus replacing one or more of the carbons. Substituted heteroalkyls are also encompassed by the term alkyl.

In some embodiments, an optionally substituted alkyl may contain, e.g., 1-20, 1-18, 1-16, 1-14, 1-12, 1-10, 1-8, 1-6, 1-4, or 1-2 carbon atoms, not including the carbon atoms present in the substituents if the alkyl is substituted. In some embodiments, an optionally substituted alkenyl or an optionally substituted alkynyl may contain, e.g., 2-20, 2-18, 2-16, 2-14, 2-12, 2-10, 2-8, 2-6, or 2-4 carbon atoms, not including the carbon atoms present in the substituents if the alkenyl or alkynyl is substituted.

Alkylamino: a heteroalkyl wherein one or more of the carbon atoms is replaced with a nitrogen. An alkylamino can be a straight chain, branched, or cycloalkylamino. An alkylamino generally has the structure —$NX_1X_2$ or —$NX_1X_2X_3^+$ in which $X_1$, $X_2$, and $X_3$ are each independently selected from, e.g., H, an optionally substituted alkyl (e.g., a substituted alkyl or an unsubstituted alkyl, as the term is defined above), an optionally substituted alkenyl (e.g., an optionally substituted $C_{2-6}$ alkenyl), an optionally substituted alkynyl (e.g., an optionally substituted $C_{2-6}$ alkynyl), an optionally substituted cycloalkyl (e.g., an optionally substituted $C_{3-6}$ cycloalkyl), an optionally substituted heterocyclyl ring (e.g., an optionally substituted 3- to 6-membered heterocyclyl ring containing one heteroatom selected from O, N, and S), an optionally substituted aryl (e.g., a phenyl group optionally substituted by 1, 2, or 3 substituents each independently selected from the group consisting of OH, NO$_2$, and halogen), an optionally substituted —O—C$_{1-6}$ alkyl (e.g., —O—C$_{1-6}$ alkyl optionally substituted by 1, 2, or 3 substituents each independently selected from OH, halogen, NH$_2$, —NH(C$_{1-6}$ alkyl), —N(C$_{1-6}$ alkyl)$_2$, —SO$_2$H, —SO$_2$(C$_{1-6}$ alkyl), CN, C$_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, NO$_2$, and halogen), an acyl, OH, NH$_2$, —NH(C$_{1-6}$ alkyl), —N(C$_{1-6}$ alkyl)$_2$, —SO$_2$H, or —SO$_2$(C$_{1-6}$ alkyl).

In some embodiments, an alkylamino has the structure —NX$_1$X$_2$ in which X$_1$ is H or an optionally substituted C$_{1-6}$ alkyl and X$_2$ is a C$_{1-6}$ alkyl optionally substituted by 1, 2, or 3 substituents each independently selected from OH, halogen, NH$_2$, —NH(C$_{1-6}$ alkyl), —N(C$_{1-6}$ alkyl)$_2$, —SO$_2$H, —SO$_2$(C$_{1-6}$ alkyl), CN, C$_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, NO$_2$, and halogen.

In some embodiments, an alkylamino has the structure —NX$_1$X$_2$ in which X$_1$ is H or an optionally substituted C$_{1-6}$ alkyl and X$_2$ is —O—C$_{1-6}$ alkyl optionally substituted by 1, 2, or 3 substituents each independently selected from OH, halogen, NH$_2$, —NH(C$_{1-6}$ alkyl), —N(C$_{1-6}$ alkyl)$_2$, —SO$_2$H, —SO$_2$(C$_{1-6}$ alkyl), CN, C$_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, NO$_2$, and halogen.

In some embodiments, an alkylamino has the structure —NX$_1$X$_2$ in which X$_1$ is H or an optionally substituted C$_{1-6}$ alkyl and X$_2$ is a phenyl group optionally substituted by 1, 2, or 3 substituents each independently selected from the group consisting of OH, NO$_2$, and halogen.

In some embodiments, an alkylamino has the structure —NX$_1$X$_2$ in which X$_1$ and X$_2$ are each independently selected from H, substituted aliphatic, unsubstituted aliphatic, substituted phenyl, unsubstituted phenyl, OR$^{N1}$, —N(R$^{N1}$)$_2$, or —SO$_2$(R$^{N2}$), wherein each R$^{N1}$ is independently H, substituted aliphatic, or unsubstituted aliphatic, and R$^{N2}$ is OH, unsubstituted aliphatic, or substituted aliphatic. In some embodiments, if one R$^N$ is OR$^{N1}$, —N(R$^{N1}$)$_2$, or —SO$_2$(R$^{N2}$), the other R$^N$ is H, substituted aliphatic, unsubstituted aliphatic, substituted phenyl, or unsubstituted phenyl.

In some embodiments, an alkylamino has the structure —NX$_1$X$_2$ in which X$_1$ is H and X$_2$ is H, hydroxyl, amino, methyl, ethyl, propyl, cyclopropyl, 2-hydroxyethyl, 1-hydroxypropan-2-yl, 2-hydroxypropyl, 2-aminoethyl acetate, 2-fluoroethyl, 2,2-difluoroethyl, 2,2,2-trifluoroethyl, phenyl, (4-nitro)phenyl, 2-phenylethyl 2-(2-hydroxyphenyl)ethyl, 2-(3-hydroxyphenyl)ethyl, 2-(3,4-dihydroxyphenyl)ethyl, 3-fluoroethyl; S-methylsulfonyl, 1-(2-hydroxyethyl)-2-hydroxyethyl, 2-propenyl, 2-propynyl, methoxy, 2-ethylsulfonate sodium, cyanomethyl, or oxetanyl.

Examples of alkylamino groups include, but are not limited to, the following structures: —NHCH$_3$, —N(CH$_3$)$_2$, —NH(CH$_3$)$_2$+, —N(CH$_3$)$_3$+, —NHCH$_2$CH$_3$, —NH$_2$CH$_2$CH$_3$+, —NCH$_3$CH$_2$CH$_3$, —N(CH$_2$CH$_3$)$_2$, and —NHCH$_3$CH$_2$CH$_3$+. Alkylamino also encompasses heteroalkyls in which one or more of the carbon atoms is replaced with a nitrogen and/or, in addition, one or more of the other carbon atoms is replaced with another heteroatom such as oxygen, sulfur, or phosphorus.

The term alkylamino also contemplates alkyl groups bonded to the nitrogen forming a bond with non-terminal carbons to form a cycloalkylamino structure, for example X$_1$NHX$_3$ wherein X$_1$ and X$_3$ are alkyl groups that form a covalent bond with one another. These include 4-member single nitrogen (azetidinyl), 5-member single nitrogen (pyrrolidinyl), or 6-member single nitrogen (piperidinyl) structures, as well as double nitrogen structures, substituted cycloalkylamino structures, including X$_1$NX$_2$X$_3$ wherein X, and X$_3$ form a covalent bond and X$_2$ is alkyl. Alkylamino groups are further exemplified by a CH$_2$CH$_2$—NHR$_2$ structure wherein R$_2$ is ethyl and forms a covalent bond with the first carbon to form a 4-member ring.

Amide: a group of the structure —CH$_2$—CONX$_1$X$_2$, wherein X, and X$_2$ are each independently H or an organic group such as an optionally substituted alkyl or an optionally substituted aryl group. In some embodiments, an amide has the structure —CH$_2$—CONX$_1$X$_2$, wherein X$_1$ and X$_2$ are each independently H, an optionally substituted alkyl (e.g., a substituted alkyl or an unsubstituted alkyl, as the term is defined above), an optionally substituted alkenyl (e.g., an optionally substituted C$_{2-6}$ alkenyl), an optionally substituted alkynyl (e.g., an optionally substituted C$_{2-6}$ alkynyl), an optionally substituted cycloalkyl (e.g., an optionally substituted C$_{3-6}$ cycloalkyl), an optionally substituted heterocyclyl ring (e.g., an optionally substituted 3- to 6-membered heterocyclyl ring containing one heteroatom selected from O, N, and S), an optionally substituted aryl (e.g., a phenyl group optionally substituted by 1, 2, or 3 substituents each independently selected from the group consisting of OH, NO$_2$, and halogen), an optionally substituted —O—C$_{1-6}$ alkyl (e.g., —O—C$_{1-6}$ alkyl optionally substituted by 1, 2, or 3 substituents each independently selected from OH, halogen, NH$_2$, —NH(C$_{1-6}$ alkyl), —N(C$_{1-6}$ alkyl)$_2$, —SO$_2$H, —SO$_2$(C$_{1-6}$ alkyl), CN, C$_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, NO$_2$, and halogen), an acyl, OH, NH$_2$, —NH(C$_{1-6}$ alkyl), —N(C$_{1-6}$ alkyl)$_2$, —SO$_2$H, or —SO$_2$(C$_{1-6}$ alkyl).

Amino: a group of the structure —N(R$^N$)$_2$, where each R$^N$ is independently H, substituted aliphatic, unsubstituted aliphatic, substituted phenyl, unsubstituted phenyl, —OR$^{N1}$, —N(R$^{N1}$)$_2$, or —SO$_2$(R$^{N2}$), where each R$^{N1}$ is independently H, substituted aliphatic, or unsubstituted aliphatic, and R$^{N2}$ is —OH, unsubstituted aliphatic, or substituted aliphatic; provided that, if one R$^N$ is —OR$^{N1}$, —N(R$^{N1}$)$_2$, or —SO$_2$(R$^{N2}$), the other R$^N$ is H, substituted aliphatic, unsubstituted aliphatic, substituted phenyl, or unsubstituted phenyl.

Aryl: any carbon-based aromatic group including, but not limited to, benzene, naphthalene, and phenyl. The term aryl also contemplates substituted aryls in which one or more of the hydrogens is substituted with one or more groups including but not limited to alkyl, alkynyl, alkenyl, aryl, halide, nitro, amino, ester, ether, ketone, aldehyde, hydroxy, carboxylic acid, cyano, amido, haloalkyl, haloalkoxy, or alkoxy. The term aryl also contemplates heteroaryls in which one or more of the carbons is replaced by a heteroatom. Examples of heteroatoms include, but are not limited to, nitrogen, oxygen, sulfur, and phosphorous. Substituted heteroaryls are also encompassed by the term aryl. A substituted phenyl is a phenyl group substituted with 1, 2, 3, 4, or 5 substituents independently selected from —OR, —NO$_2$, unsubstituted aliphatic, and halogen, where R is H or unsubstituted aliphatic. An aryl refers to any monocyclic or fused ring bicyclic or tricyclic system which has the characteristics of aromaticity in terms of electron distribution throughout the ring system, e.g., phenyl, naphthyl, or phenanthrene. In some embodiments, a ring system contains 5 15 ring member atoms or 5-10 ring member atoms. An aryl group may have, e.g., between five to fifteen carbons (e.g., a $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, or $C_{5-15}$ aryl).

Acyl: a group having the structure:

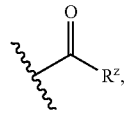

wherein $R^z$ is an optionally substituted alkyl, alkenyl, alkynyl, cycloalkyl, cycloalkenyl, cycloalkynyl, aryl, heteroalkyl, heteroalkenyl, heteroalkynyl, heterocycloalkyl, heterocycloalkenyl, heterocycloalkynyl, or heteroaryl.

Cycloalkyl: a non-aromatic carbon-based ring composed of at least three carbon atoms. Examples of cycloalkyl groups include, but are not limited to, cyclopropyl, cyclobutyl, cyclopentyl, and cyclohexyl. Cycloalkyls also encompass substituted cycloalkyls and heterocycloalkyls (also referred to as "heterocyclyl" groups) where at least one of the carbon atoms is replaced with a heteroatom such as nitrogen, sulfur, oxygen, or phosphorus. A heterocycloalkyl wherein one or more of the carbons is replaced with nitrogen is also termed a cycloalkylamino herein. The term also encompasses substituted heterocycloalkyls. Oxygen-containing heterocyclyl groups for use in the embodiments herein include, but are not limited to, oxiranyl, oxetanyl, tetrahydrofuranyl, and tetrahydropyranyl groups.

Optionally substituted: a group (e.g., an alkyl, alkenyl, alkynyl, cycloalkyl, or aryl) having 0, 1, or more substituents, such as 0-25, 0-20, 0-10 or 0-5 substituents. Substituents include, but are not limited to, alkyl, alkenyl, alkynyl, aryl, alkaryl, acyl, heteroaryl, heteroalkyl, heteroalkenyl, heteroalkynyl, heteroalkaryl, halogen, oxo, cyano, nitro, amino, alkamino, hydroxy, alkoxy, alkanoyl, carbonyl, carbamoyl, guanidinyl, amidinyl, ureido, any of the groups or moieties described above, and hetero versions of any of the groups or moieties described above. Substituents include, but are not limited to, F, Cl, methyl, phenyl, benzyl, OR, NR$_2$, SR, SOR, SO$_2$R, OCOR, NRCOR, NRCONR$_2$, NRCOOR, OCONR$_2$, RCO, COOR, alkyl-OOCR, SO$_3$R, CONR$_2$, SO$_2$NR$_2$, NRSO$_2$NR$_2$, CN, CF$_3$, OCF$_3$, R$_3$Si, and NO$_2$, wherein each R is, independently, H, alkyl, alkenyl, aryl, heteroalkyl, heteroalkenyl, or heteroaryl, and wherein two of the optional substituents on the same or adjacent atoms can be joined to form a fused, optionally substituted aromatic or nonaromatic, saturated or unsaturated ring which contains 3-8 members.

Effective amount, therapeutically effective amount, or pharmaceutically effective amount: a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

Derivative: a compound or portion of a compound that is derived from or is theoretically derivable from a parent compound.

Hemorrhage: Bleeding or escape of blood from a vessel.

Hypoxia: The lack of oxygen supply to the tissues of the body below the normal level.

Heterocycle: A group that encompasses both heteroaryls and heterocycloalkyls heterocycles may be monocyclic or polycyclic rings. Exemplary heterocycles include, but are not limited to, azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups. The term also contemplates substituted heterocycles, including substituted forms of all the species above.

Injury: Refers to any type of physical damage to cells, tissues, or the body. In some cases, nervous system (e.g., CNS or PNS) injury results in demyelination and/or a demyelinating disease.

Ischemia: A vascular phenomenon in which a decrease in the blood supply to a bodily organ, tissue, or part is caused, for instance, by constriction or obstruction of one or more blood vessels.

Ischemia sometimes results from vasoconstriction, thrombosis or embolism. Ischemia can lead to direct ischemic injury, tissue damage due to cell death caused by reduced oxygen supply. In some cases, ischemia can lead to demyelination.

Myelin: A lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

Pharmaceutical composition: A composition containing a pharmaceutically effective amount of one or more of the compounds described herein, or a pharmaceutically acceptable salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

Pharmaceutically acceptable carrier: Any ingredient other than the disclosed compounds, or a pharmaceutically acceptable salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Pharmaceutically acceptable salt: Salts prepared by conventional methods. These include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. "Pharmaceutically acceptable salts" of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms of the disclosed compounds. Descriptions of exemplary pharmaceutically acceptable salts can be found in Stahl and Wermuth, Eds., *Handbook of Pharmaceutical Salts; Properties, Selection and Use*, Wiley VCH (2008). When the compounds disclosed herein include an acidic group such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. Similarly when the compounds disclosed herein include a basic group such as an amino group, then suitable pharmaceutically acceptable anion pairs for the basic group are similarly well known and include halide, hydroxide, perhalate, halite, hypohalite, sulfate, sulfite, phosphate, phosphite, nitrate, nitrite, and others known to those of skill in the art. For additional examples of pharmacologically acceptable salts, see Berge et al, *J. Pharm. Sci.* 66, 1 (1977).

Sobetirome: A synthetic diarylmethane compound that was investigated clinically as a potential therapeutic for hypercholesterolemia (see U.S. Pat. No. 5,883,294, which is incorporated by reference herein). Sobetirome is 2-[4-[[4-hydroxy-3-(1-methyletheyl)phenyl]methyl]3,5-dimethylphenoxy acetic acid. Other names for sobetirome found in the literature and regulatory filings include QRX-431 and GC-1.

Subject: An animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

Treatment: an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

Neurodegenerative Diseases:

Acute disseminated encephalomyelitis (ADEM): An immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

Acute hemorrhagic leukoencephalitis (AHL or AHLE): A hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

Adult Refsum disease: An autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

Alexander disease: A very rare, congenital demyelinating disease. The disease primarily affects infants and children, causing developmental delay and changes in physical characteristics. Alexander disease is a type of leukodystrophy.

Alzheimer's disease: The most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypotheses exist, including that the disease is caused by age-related myelin breakdown in the brain.

Balo concentric sclerosis: A demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

Canavan disease: An autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

Central pontine myelinolysis (CPM): A neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

Cerebral palsy: A term used for a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

Cerebrotendineous xanthomatosis: An inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

Chronic inflammatory demyelinating polyneuropathy (CIDP): An acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barré syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

Demyelinating disease: Includes any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

Devic's syndrome: An autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's syndrome is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's syndrome or neuromyelitis optica (NMO).

Diffuse myelinoclastic sclerosis: An uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

Encephalomyelitis: Inflammation of the brain and spinal cord.

Experimental autoimmune encephalomyelitis (EAE): An animal model of MS (for example, see Gold et al, Brain 129, 1953-1971 (2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases, EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

Guillain-Barré syndrome: An acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

Idiopathic inflammatory demyelinating disease (IIDD): A broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

Infantile Refsum disease: A peroxisome biogenesis disorder associated with deficiencies in the catabolism of very long chain fatty acids and branched chain fatty acids (such as phytanic acid) and plasminogen biosynthesis. Infantile Refsum disease is a rare, autosomal recessive congenital disorder, and one of three peroxisome biogenesis disorders that belong to the Zellweger spectrum of peroxisome biogenesis disorders.

Krabbe disease: A rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

Leber hereditary optic neuropathy: A mitochondrially inherited (transmitted from mother to offspring) degeneration of retinal ganglion cells (RGCs) and their axons that leads to an acute or subacute loss of central vision; this affects predominantly young adult males.

Leukodystrophy: Refers to a group of diseases that affects the growth or development of the myelin sheath.

Leukoencephalopathy: Any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

Marburg multiple sclerosis: A condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

Marchiafava-Bignami disease: A progressive neurological disease characterized by corpus callosum demyelination and necrosis and subsequent atrophy. It is classically associated with chronic alcoholics.

Metachromatic leukodystrophy (MLD): A lysosomal storage disease that is commonly listed in the family of leukodystrophies, as well as in the sphingolipidoses as it affects the metabolism of sphingolipids. MLD is directly caused by a deficiency of the enzyme arylsulfatase A.

Multifocal motor neuropathy (MMN): A progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

Multiple sclerosis (MS): A slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

Neurodegenerative disease: Refers to any type of disease that is characterized by the progressive deterioration of the nervous system.

Neuropathy: A functional disturbance or pathological change in the peripheral nervous system. Axonal neuropathy refers to a disorder disrupting the normal functioning of the axons.

Paraproteinemic demyelinating polyneuropathy: A type of peripheral neuropathy characterized by auto antibodies directed against myelin associated glycoproteins (MAG). Anti-MAG antibodies inhibit the production of myelin, thereby leading to neuropathy.

Pelizaeus-Merzbacher disease (PMD): A rare central nervous system disorder in which coordination, motor abilities, and intellectual function are delayed to variable extents. The disease is one in a group of genetic disorders collectively known as leukodystrophies.

Peroneal muscular atrophy (PMA): A genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

Progressive multifocal leukoencephalopathy (PML): A rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

Transverse myelitis: A neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

Tropical spastic paraparesis (TSP): An infection of the spinal cord by human T-lymphotropic virus resulting in paraparesis, weakness of the legs. TSP is also known as HTLV associated myelopathy or chronic progressive myelopathy. As the name suggests, this disease is most common in tropical regions, including the Caribbean and Africa.

Van der Knaap disease: A form of hereditary CNS demyelinating disease. This disease is a type of leukodystrophy and is also known as megalencephalic leukoencephalopathy with subcortical cysts (MLC).

X-linked adrenoleukodystrophy (X-ALD, ALD, or X-linked ALD): A rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

Zellweger syndrome: A rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

Amide Compounds of the Invention

Systemically administered sobetirome distributes predominantly to the liver. There is indirect evidence from several prior studies indicating that sobetirome distribute to the CNS (Takahashi N et al, *Biol Pharm Bull* 37, 1103-1108 (2014); Trost S et al, *Endocrinology* 141, 3057-3064 (2000), Bernal J, *Nat Clin Pract Endrocrinol Metab* 3, 249-259 (2007); Oppenheimer J H and Schwartz H L, *Endocr Rev* 18, 462-475 (1997); and Bernal J, *J Endocrinol Invest* 25, 268-288 (2002); all of which are incorporated by reference herein).

Generally, brain/serum ratio in the range of 0.3-1.0 is often preferable for CNS drugs (Doran A et al, *Drug Metab Dispos* 33, 165-174 (2005) and Reichel A, *Curr Drug Metab* 7, 183-203 (2006); both of which are incorporated by reference herein). A compound of the invention may exhibit improved blood-brain barrier (BBB) penetration, as measured by the brain/serum ratio. In a non-limiting example, a compound of the invention may provide a brain/serum ratio of at least 0.3 (e.g., at least 0.4 or at least 0.5). These compounds may exhibit reduced or no GC-1-like activity in peripheral tissue. Without wishing to be bound by theory, a compound of the invention may be unmasked in the CNS by resident hydrolases to produce GC-1, thereby producing high in-CNS GC-1 concentrations (FIG. 1). GC-1 may become ion-trapped in the CNS, thereby producing allowing for therapeutic effect in the CNS (e.g., remyelination). A higher brain/serum ratio for the compounds of the invention may advantageously produce reduced or no peripheral action.

U.S. Nonprovisional patent application Ser. No. 15/048, 672, incorporated by reference herein, describes ester compounds that, upon hydrolysis, can produce sobetirome (GC-1). Ester compounds including 2-aminoethanol ester motif were observed to cross the blood-brain barrier efficiently. Under certain physiological conditions, these compounds may undergo a rearrangement to the corresponding amide product (Scheme 1). Analysis of the amide products revealed that elevated brain GC-1 levels were attributable to this amide conversion product rather than the parent ester compounds. The compounds of the invention were developed and are disclosed herein.

Scheme 1 - sobetirome aminoethanol ester converts to an amide in vivo.

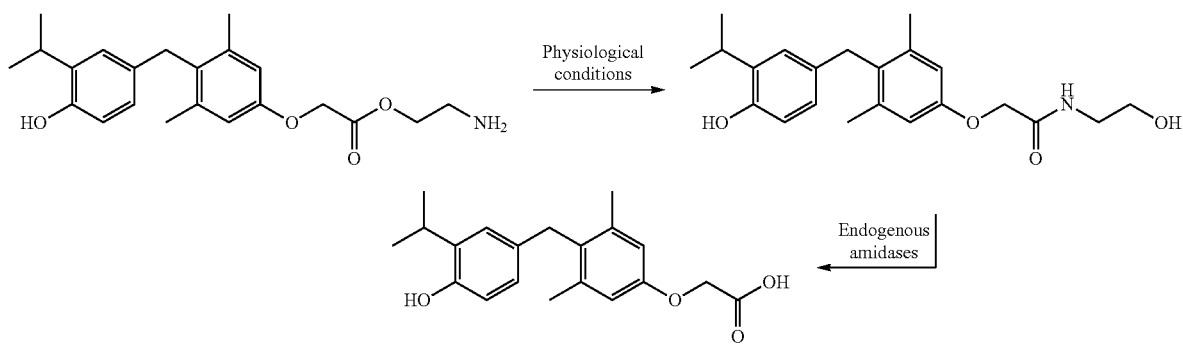

The compounds of the invention may exhibit increased chemical and biological stability relative to esters. They are likely are less prone to spontaneous hydrolysis demonstrated by aqueous hydrolysis (for a discussion of hydrolysis rates, see Mabey W & Mill T, *J Phys Chem Ref Data* 7, 383-415 (1978)). Additionally, other compounds may be subject to the action of large families of enzymes in vivo (Fukami T and Yokoi T, *Drug Metab Pharmacokinet* 27, 466-477 (2012); Casey Laizure S et al, *Pharmacotherapy* 33, 210-222 (2013); all of which are incorporated by reference herein) that can lead to premature hydrolysis. The hydrolysis of the compounds of the invention may be specific to certain brain-resident amidases. Without wishing to be bound by theory, enzymatic cleavage of non-peptidic amides can be more restricted in scope than for other compounds.

Disclosed are compounds of Formula I:

Formula I

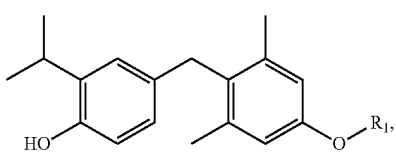

or a pharmaceutically acceptable salt thereof, wherein $R_1$ is an amide.

Also disclosed are compounds of Formula II:

Formula II

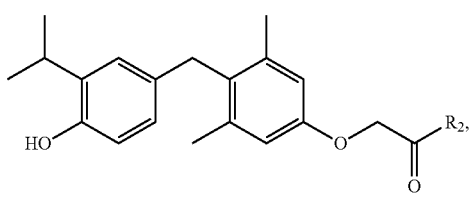

or a pharmaceutically acceptable salt thereof, wherein $R_2$ is alkylamino or amino.

Also disclosed are compounds of Formula III:

Formula III

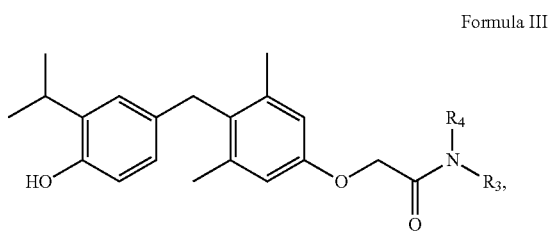

or a pharmaceutically acceptable salt thereof, wherein each of $R_3$ and $R_4$ is as described in detail herein.

Also disclosed are compounds of Formula IV:

Formula IV

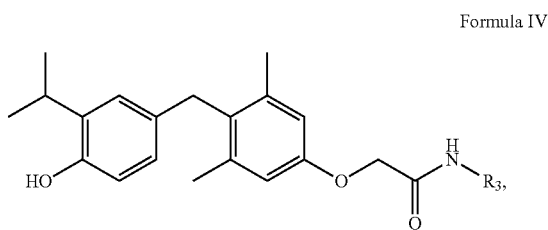

or a pharmaceutically acceptable salt thereof, wherein $R_3$ is as described in detail herein.

Further, the disclosure includes a pharmaceutical composition including a pharmaceutically effective amount of a compound described herein, or a pharmaceutically acceptable salt thereof, and one or more pharmaceutically acceptable carriers.

Methods of Treatment

It is understood that each of the compounds described herein, or a pharmaceutically acceptable salt thereof, may be used in a method of treatment of each of the maladies or diseases referenced herein. Each method of treatment comprises administering to a subject in need thereof, such as a human in need thereof, a pharmaceutically effective amount of a compound as described herein, or a pharmaceutically acceptable salt thereof.

For instance, provided is a method of treating a neurodegenerative disease in a subject, such as a human subject, the method comprising administering to the subject a pharmaceutically effective amount of a compound herein, or a pharmaceutically acceptable salt thereof.

Also provided is a method of treating a demyelinating disease in a subject, such as a human subject, the method comprising administering to the subject a pharmaceutically effective amount of a compound herein, or a pharmaceutically acceptable salt thereof.

Further provided is a method of treating X-linked adrenoleukodystrophy in a subject, such as a human subject, the method comprising administering to the subject a pharmaceutically effective amount of a compound herein, or a pharmaceutically acceptable salt thereof.

Further provided is a method of treating multiple sclerosis in a subject, such as a human subject, the method comprising administering to the subject a pharmaceutically effective amount of a compound herein, or a pharmaceutically acceptable salt thereof.

Further provided is a method of treating Alzheimer's disease in a subject, such as a human subject, the method comprising administering to the subject a pharmaceutically effective amount of a compound herein, or a pharmaceutically acceptable salt thereof.

Also provided is a method of treatment for a disease or condition selected from the group consisting of Acute disseminated encephalomyelitis (ADEM), Acute hemorrhagic leukoencephalitis (AHL or AHLE), Adult Refsum disease, Infantile Refsum disease, Alexander disease, Alzheimer's disease, Balo concentric sclerosis, Canavan disease, Central pontine myelinolysis (CPM), Cerebral palsy, Cerebrotendineous xanthomatosis, Chronic inflammatory demyelinating polyneuropathy (CIDP), Devic's syndrome, Diffuse myelinoclastic sclerosis, Encephalomyelitis, Guillain-Barré syndrome, Idiopathic inflammatory demyelinating disease (IIDD), Krabbe disease, Leber hereditary optic neuropathy, Leukodystrophy, Marburg multiple sclerosis, Marchiafava-Bignami disease, Metachromatic leukodystrophy (MLD), Multifocal motor neuropathy (MMN), Multiple sclerosis (MS), Paraproteinemic demyelinating polyneuropathy, Pelizaeus-Merzbacher disease (PMD), Progressive multifocal leukoencephalopathy (PML), Tropical spastic paraparesis (TSP), X-linked adrenoleukodystrophy (X-ALD, ALD, or X-linked ALD), and Zellweger syndrome. The method comprises administering to a subject in need thereof, such as a human subject, a pharmaceutically effective amount of a compound described herein, or a pharmaceutically acceptable salt thereof.

It is also understood that each of the compounds described herein, or a pharmaceutically acceptable salt thereof, may be used in the preparation of a medicament useful in the treatment of each of the maladies or diseases referenced herein. Each method of treatment comprises administering to a subject in need thereof, such as a human in need thereof, a pharmaceutically effective amount of a compound as described herein, or a pharmaceutically acceptable salt thereof.

For instance, provided is the use of a compound described herein, or a pharmaceutically acceptable salt thereof, in the preparation of a medicament useful in the treatment of a neurodegenerative disease in a subject, such as a human subject.

For instance, provided is the use of a compound described herein, or a pharmaceutically acceptable salt thereof, in the preparation of a medicament useful in the treatment of a demyelinating disease in a subject, such as a human subject.

For instance, provided is the use of a compound described herein, or a pharmaceutically acceptable salt thereof, in the preparation of a medicament useful in the treatment of adrenoleukodystrophy in a subject, such as a human subject.

For instance, provided is the use of a compound described herein, or a pharmaceutically acceptable salt thereof, in the preparation of a medicament useful in the treatment of multiple sclerosis in a subject, such as a human subject.

For instance, provided is the use of a compound described herein, or a pharmaceutically acceptable salt thereof, in the preparation of a medicament useful in the treatment of Alzheimer's disease in a subject, such as a human subject.

Also provided is the use of a compound as described herein, or a pharmaceutically acceptable salt thereof, for the preparation of a medicament useful in the treatment of a disease or condition in a subject, such as a human subject, selected from the group consisting of Acute disseminated encephalomyelitis (ADEM), Acute hemorrhagic leukoencephalitis (AHL or AHLE), Adult Refsum disease, Infantile Refsum disease, Alexander disease, Alzheimer's disease, Balo concentric sclerosis, Canavan disease, Central pontine myelinolysis (CPM), Cerebral palsy, Cerebrotendineous xanthomatosis, Chronic inflammatory demyelinating polyneuropathy (CIDP), Devic's syndrome, Diffuse myelinoclastic sclerosis, Encephalomyelitis, Guillain-Barré syndrome, Idiopathic inflammatory demyelinating disease (IIDD), Krabbe disease, Leber hereditary optic neuropathy, Leukodystrophy, Marburg multiple sclerosis, Marchiafava-Bignami disease, Metachromatic leukodystrophy (MLD), Multifocal motor neuropathy (MMN), Multiple sclerosis (MS), Paraproteinemic demyelinating polyneuropathy, Pelizaeus-Merzbacher disease (PMD), Progressive multifocal leukoencephaalopathy (PML), Tropical spastic paraparesis (TSP), X-linked adrenoleukodystrophy (X-ALD, ALD, or X-linked ALD), and Zellweger syndrome.

EXAMPLES

The following examples are for illustration only. In light of this disclosure, those of skill in the art will recognize that variations of these examples and other examples of the disclosed invention be possible without undue experimentation.

Example 1—Animal Studies

Experimental protocols were in compliance with the National Institutes of Health Guide for the Care and Use of Laboratory Animals and approved by the Oregon Health & Science University Institutional Animal Care & Use Committee. Wild type male C57Bl/6 mice, aged 8-10 weeks, were housed in a climate-controlled room with a 12 hour light-dark cycle with ad libitum access to food and water. For the single time-point analysis of GC-1 concentrations in vivo, mice were injected once intraperitoneally (i.p.) with sobetirome and prodrugs at 3.05 µmol/kg. Euthanasia was performed on three mice after 1 hour and the tissues and blood were harvested. Tissues were immediately frozen and blood was kept on ice for a minimum of 30 minutes and then spun down at 7,500×G for 15 minutes. Serum (100 µL) was collected and was stored with tissues at −80° C. until samples were processed. Serum Processing: The serum samples were warmed to room temperature and 10 µL of 2.99 µM internal standard (d6-Sobetirome) was added to them. Acetonitrile (500 µL) was added and the sample was vortexed for 20 seconds. The sample was then centrifuged at 10,000×G for 15 minutes at 4° C. Next, 90% of the upper supernatant was transferred to a glass test tube and concentrated using a speedvac for 1.5 hours at 45° C. The dried sample was then dissolved in 400 µL of 50:50 acetonitrile: $H_2O$ and vortexed for 20 seconds. The resulting mixture was transferred to an Eppendorf and centrifuged at 10,000×G for 15 minutes. The supernatant was filtered with 0.22 μM centrifugal filters and submitted for LC-MS/MS analysis to quantify the amount of free sobetirome. The standard curve was made with 100 μL of serum from an 8-10 week old mouse that had received a vehicle-only injection. The processing was performed exactly the same except after filtering the sample was split amongst 6 vials. To 5 out of the 6 vials was added sobetirome to make final concentrations in matrix of (0.1 pg/μL, 1 pg/μL, 10 pg/μL, 100 pg/μL, and 1000 pg/μL).

Brain Processing: The brain samples were warmed to room temperature and transferred to a homogenizer tube with GoldSpec 1/8 chrome steel balls (Applied Industrial Technologies). The resulting tube was weighed and then 1 mL of $H_2O$ was added, followed by 10 μL of 2.99 μM internal standard (d6-sobetirome). The tube was homogenized with a Bead Bug® for 30 seconds and then transferred to a Falcon tube containing 3 mL of acetonitrile. Acetonitrile (1 mL) was used to wash homogenizer tube and the solution was transferred back to the Falcon tube. The sample was then processed using the same method for the serum processing except the sample was concentrated in a glass tube using a speedvac for 4 hours at 45° C. The samples were then processed using the serum processing method for LC-MS/MS analysis.

Results are shown in Table 1.

TABLE 1

| | Brain | | Serum | | Brain/Serum | |
|---|---|---|---|---|---|---|
| Cpd # | GC-1 (ng/g) | SEM | GC-1 (ng/g) | SEM | GC-1 | SEM |
| GC-1 | 3.58 | 0.22 | 318.55 | 112.08 | 0.030 | 0.001 |
| 1 | 25.52 | 6.34 | 66.80 | 4.64 | 0.37 | 0.06 |
| 2 | 22.29 | 1.71 | 33.73 | 5.49 | 0.69 | 0.09 |
| 3 | 38.71 | 4.99 | 55.73 | 10.92 | 0.72 | 0.08 |
| 4 | 0.77 | 0.77 | 6.93 | 1.94 | 0.07 | 0.07 |
| 5 | 93.90 | 37.11 | 79.48 | 25.95 | 1.17 | 0.45 |
| 6 | 125.39 | 26.81 | 128.77 | 43.07 | 1.04 | 0.11 |
| 7 | 59.42 | 6.66 | 80.18 | 14.20 | 0.76 | 0.09 |
| 8 | 53.08 | 7.35 | 17.17 | 3.44 | 3.17 | 0.30 |
| 9 | 7.45 | 5.07 | 174.74 | 112.72 | 0.04 | 0.01 |
| 10 | 12.83 | 1.72 | 325.71 | 66.04 | 0.04 | 0.00 |
| 11 | 1.58 | 0.56 | 26.15 | 8.16 | 0.06 | 0.01 |
| 12 | 2.56 | 0.96 | 98.03 | 41.17 | 0.03 | 0.01 |
| 13 | 20.24 | 9.02 | 16.91 | 4.34 | 1.15 | 0.56 |
| 14 | 107.09 | 9.47 | 64.19 | 8.51 | 1.70 | 0.13 |
| 15 | 33.42 | 13.75 | 25.38 | 3.38 | 1.23 | 0.35 |
| 16 | 59.49 | 14.27 | 59.36 | 4.65 | 0.99 | 0.19 |
| 17 | 8.38 | 0.35 | 209.73 | 31.00 | 0.04 | 0.00 |
| 18 | 7.39 | 6.72 | 4.88 | 2.12 | 0.94 | 0.82 |
| 19 | 11.27 | 0.46 | 8.63 | 0.31 | 1.31 | 0.05 |
| 20 | 2.79 | 0.44 | 127.74 | 50.36 | 0.03 | 0.01 |
| 21 | 68.25 | 40.50 | 199.51 | 87.37 | 0.58 | 0.28 |
| 22 | 4.61 | 0.74 | 212.33 | 114.80 | 0.05 | 0.03 |
| 23 | 7.11 | 6.32 | 45.67 | 3.62 | 0.18 | 0.16 |

Example 2—General Chemistry $^1$H NMR were taken on a Bruker 400®. All $^1$H NMR were calibrated to the NMR solvent reference peak (DMSO-$d_6$, chloroform-d, methanol-$d_4$). High-resolution mass spectrometry (HRMS) with electrospray ionization was performed by the Bioanalytical MS Facility at Portland State University. Inert atmosphere reactions were performed under argon gas passed through a small column of drierite and were conducted in flame-dried rbfs. Anhydrous tetrahydrofuran (THF), dichloromethane (DCM), and dimethylformamide (DMF) were obtained from a Seca Solvent System. All other solvents used were purchased from Sigma-Aldrich or Fisher. The synthesis of Sobetirome (GC-1) has previously been described (Chiellini G et al, Bioorg Med Chem Lett 10, 2607-2611 (2000) and Placzek A T et al, Tetrahedron 71, 5946-5951 (2015); both of which are incorporated by reference herein). The synthesis of O-benzyl GC-1 (2-(4-(4-(benzyloxy)-3-isopropylbenzyl)-3,5-dimethylphenoxy)acetic acid) was previously disclosed. All other reagents were purchased from Fisher, Sigma, or TCI and used as received. Purity analysis of final compounds was determined to be >95% by HPLC. Analytical HPLC analysis was performed on a Varian ProStar HPLC with a Grace Alltima C18, 5 μm column (4.6×250 mm) with a gradient (Solvent A: 95:5 Water:MeCN, 0.2% $Et_3NH_3PO_4$, pH 2.5; Solvent B: MeCN) for B of 40% to 100% over 20 minutes with a flowrate of 1 mL/min. Preparative HPLC was performed on a Varian Dynamax Microscrob 100-5 uM C18, 21.4×250 mm (Solvent A: Water+0.1% formic acid; Solvent B: MeCN+0.1% formic acid) using a gradient of B 20-100% over 20 minutes with a flowrate of 25 mL/min.

Example 3—2-(4-(4-hydroxy-3-isopropylbenzyl)-3, 5-dimethylphenoxy)-N-(2-hydroxyethyl)acetamide (Compound 1)

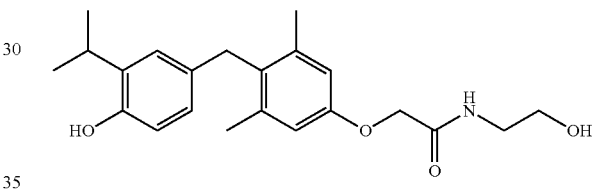

A stirring solution of 2-(4-(4-(benzyloxy)-3-isopropylbenzyl)-3,5-dimethylphenoxy)acetic acid (O-benzyl GC1, 130 mg, 0.31 mmol, 1 eq) in DCM (2 mL) at 0° C. is treated with oxalyl chloride (110 μL, 1.23 mmol, 4 eq). DMF is added (1 drop) and the reaction stirs for 3 h while warming to room temperature. The solvent is removed under reduced pressure and the crude intermediate is treated with DCM (5 mL), which is subsequently removed under reduced pressure. The crude intermediate is treated with 1.5 mL of DCM followed by dropwise addition of ethanolamine (114 mg, 1.87 mmol, 6 eq). The reaction stirs for 1 h at room temperature. The reaction mixture is purified by flash chromatography (25-100% EtOAc in hexanes) to give the intermediate product as a white solid (48 mg, 0.1 mmol, 33%). The benzyl protected intermediate (48 mg, 0.104 mmol, 1 eq) is treated with 1:1 MeOH:EtOAc (1 mL) under argon. Palladium on carbon (10 wt %, 22 mg) is added to the reaction and triethylsilane (132 μL, 0.83 mmol, 8 eq) is added dropwise. The reaction stirs overnight. An additional aliquot of triethylsilane (50 μL, 0.31 mmol, 3 eq) is added and the reaction stirs 1 h. The reaction mixture is poured over a plug of celite and washed with MeOH. The concentrated reaction solution is purified by flash chromatography (1-10% MeOH in DCM) to give the product as a white solid (29 mg, 0.076 mmol, 73%). $^1$H NMR (400 MHz, Chloroform-d) δ 7.11 (b, 1H), 6.93 (d, J=2 Hz, 1H), 6.64-6.55 (m, 4H), 5.36 (b, 1H), 4.52 (s, 2H), 3.91 (s, 2H), 3.79 (t, J=4.8 Hz, 2H), 3.55 (q, J=5.5 Hz, 2H), 3.19 (sept, J=6.9, 1H), 2.22 (s, 6H), 1.25 (d, J=6.8 Hz, 6H). HRMS (ESI) m/z [M+H+] $C_{22}H_{30}NO_4$+ requires 372.2169, found 372.2182.

Example 4—2-(4-(4-hydroxy-3-isopropylbenzyl)-3,5-dimethylphenoxy)-N-(1-hydroxypropan-2-yl)acetamide (Compound 2)

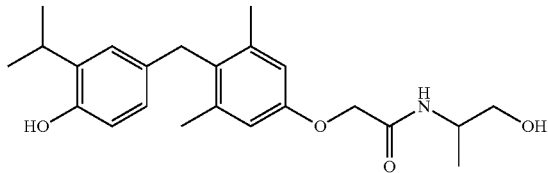 [SMILES: Cc1cc(OCC(=O)NC(C)CO)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 87 mg, 0.207 mmol, 1 eq) in DCM (1.3 mL) at 0° C. is treated with oxalyl chloride (73 μL, 0.83 mmol, 4 eq). DMF is added (1 drop) and the reaction stirs for 3 h while warming to room temperature. The solvent is removed under reduced pressure and the crude intermediate is treated with DCM (5 mL), which is subsequently removed under reduced pressure. The crude intermediate is treated with 1.5 mL of DCM followed by dropwise addition of (+/−)-alaninol (93 mg, 1.24 mmol, 6 eq). The reaction stirs for 1 h at room temperature. The reaction mixture is purified by flash chromatography (25-100% EtOAc in hexanes) to give the intermediate product as a white solid (48 mg, 0.1 mmol, 48%). The benzyl protected intermediate (40 mg, 0.085 mmol, 1 eq) is treated with 1:1 MeOH:EtOAc (1 mL) under argon. Palladium on carbon (10 wt %, 22 mg) is added to the reaction and triethylsilane (108 μL, 0.68 mmol, 8 eq) is added dropwise. The reaction stirs overnight. An additional aliquot of triethylsilane (50 μL, 0.31 mmol, 3.7 eq) is added and the reaction stirs 1 h. The reaction mixture is poured over a plug of celite and washed with MeOH. The concentrated reaction solution is purified by flash chromatography (1-10% MeOH in DCM) to give the product as a white solid (21 mg, 0.055 mmol, 64%). $^1$H NMR (400 MHz, Chloroform-d) δ 7.28 (b, 1H), 6.93 (d, J=2 Hz), 6.73-6.53 (m, 4H), 5.04 (b, 1H), 4.50 (s, 2H), 4.19 (m, 1H), 3.92 (s, 2H), 3.72-3.61 (m 2H), 3.19 (s, J=6.9 Hz, 1H), 2.65 (s, 1H), 2.24 (s, 6H), 1.23 (m, 9H). HRMS (ESI) m/z [M+H+] $C_{23}H_{32}NO_4^+$ requires 386.2326, found 386.2335.

Example 5—2-(4-(4-hydroxy-3-isopropylbenzyl)-3,5-dimethylphenoxy)-N-(2-hydroxypropyl)acetamide (Compound 3)

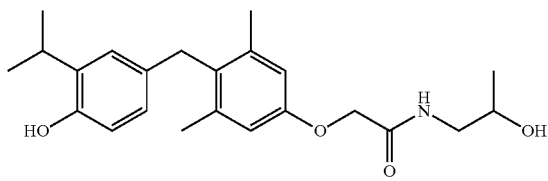 [SMILES: Cc1cc(OCC(=O)NCC(C)O)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 87 mg, 0.207 mmol, 1 eq) in DCM (1.3 mL) at 0° C. is treated with oxalyl chloride (73 μL, 0.83 mmol, 4 eq). DMF is added (1 drop) and the reaction stirs for 3 h while warming to room temperature. The solvent is removed under reduced pressure and the crude intermediate is treated with DCM (5 mL), which is subsequently removed under reduced pressure. The crude intermediate is treated with 1.5 mL of DCM followed by dropwise addition of 1-amino-2-propanol (93 mg, 1.24 mmol, 6 eq). The reaction stirs for 1 h at room temperature. The reaction mixture is purified by flash chromatography (25-100% EtOAc in hexanes) to give the intermediate product as a white solid (66 mg, 0.14 mmol, 68%). The benzyl protected intermediate (40 mg, 0.085 mmol, 1 eq) is treated with 1:1 MeOH:EtOAc (1 mL) under argon. Palladium on carbon (10 wt %, 22 mg) is added to the reaction and triethylsilane (108 μL, 0.68 mmol, 8 eq) is added dropwise. The reaction stirs overnight. An additional aliquot of triethylsilane (50 μL, 0.31 mmol, 3.7 eq) is added and the reaction stirs 1 h. The reaction mixture is poured over a plug of celite and washed with MeOH. The concentrated reaction solution is purified by flash chromatography (1-10% MeOH in DCM) to give the product as a white solid (43 mg, 0.11 mmol, 73%). $^1$H NMR (400 MHz, Chloroform-d) δ 7.11 (b, 1H), 6.93 (d, J=2 Hz), 6.61-6.51 (m, 4H), 5.84 (b, 1H), 4.49 (s, 2H), 3.96 (m, 1H), 3.91 (s, 2H), 3.51 (m, 1H), 3.19 (m, 2H), 2.27 (s, 6H), 1.20 (m, 9H). HRMS (ESI) m/z [M+H+] $C_{23}H_{32}NO_4^+$ requires 386.2326, found 386.2335.

Example 6—2-(2-(4-(4-hydroxy-3-isopropylbenzyl)-3,5-dimethylphenoxy)acetamido)ethan-1-aminium acetate (Compound 4)

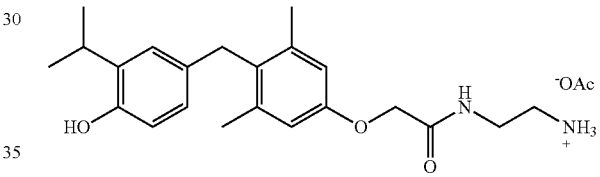

A stirring solution of 2-(4-(4-(benzyloxy)-3-isopropylbenzyl)-3,5-dimethylphenoxy)acetic acid (O-benzyl GC1, 441 mg, 1.05 mmol, 1 eq) in DCM (7 mL) at 0° C. is treated with oxalyl chloride (542 μL, 6.3 mmol, 6 eq). DMF is added (1 drop) and the reaction stirs for 3 h while warming to room temperature. The solvent is removed under reduced pressure and the crude intermediate is treated with DCM (10 mL), which is subsequently removed under reduced pressure. The crude intermediate is treated with 3 mL of DCM followed by dropwise addition of 2-aminoethyl benzyl carbamate (408 mg, 2.1 mmol, 2 eq). The reaction stirs for 1 h at room temperature. The reaction mixture is purified by flash chromatography (0-50% EtOAc in hexanes) to give the intermediate product as a white solid (380 mg, 0.643 mmol, 61%). The benzyl protected intermediate (380 mg, 0.64 mmol, 1 eq) is treated with THF (2 mL) and acetic acid (0.2 mL) under argon. Palladium on carbon (10 wt %, 270 mg) is added to the reaction and triethylsilane (818 μL, 5.11 mmol, 8 eq) is added dropwise. The reaction stirs overnight. The reaction mixture is poured over a plug of celite and washed with MeOH. The solution is concentrated and then taken up in a minimal amount of DCM and MeOH and reconcentrated under reduced pressure. The crude product is retreated with DCM (0.25 mL) with several drops of MeOH. Hexanes (3 mL) is slowly added to the solution, which leads to precipitation of the product. The hexane supernatant is removed by pipette and the white product is washed with hexanes and extensively dried under reduced pressure to give a white, viscous solid product (57 mg, 0.132 mmol, 21%). $^1$H NMR (400 MHz, d6-DMSO) δ 8.40 (b, 1H), 6.83

(d, J=2 Hz, 1H), 6.82-6.44 (m, 4H), 4.42 (s, 2H), 3.71 (s, 2H), 3.31 (t, J=6 Hz, 2H), 3.19 (sept, J=6.9 Hz, 1H), 2.79 (m, 2H), 2.16 (s, 6H), 1.83 (s, 3H), 1.09 (d, J=6.9 Hz, 6H). HRMS (ESI) m/z [M+H+] $C_{22}H_{31}N_2O_3^+$ requires 371.2335, found 371.2329.

Example 7—2-(4-(4-hydroxy-3-isopropylbenzyl)-3,5-dimethylphenoxy)acetamide (Compound 5)

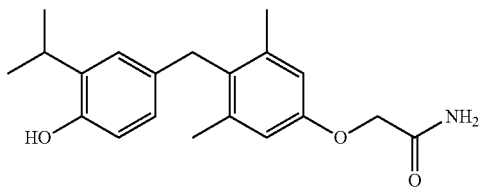 [SMILES: Cc1cc(OCC(N)=O)cc(C)c1Cc1ccc(O)c(C(C)C)c1]

GC-1 (250 mg, 0.76 mmol, 1 eq) is treated with MeOH (3 mL) in a sealed tube. Sulfuric acid (1 drop) is added and the reaction is sealed and then heated to 65° C. for 1 hour while stirring. The reaction is allowed to come to room temperature. TLC analysis (1:30 MeOH:DCM) shows complete conversion to the intermediate methyl ester. To the intermediate reaction mixture, ammonia (7N in MeOH, 0.76 mL, 7 eq) is added. The reaction is resealed and, again, heated to 65° C. for 1 hour. The reaction flask is allowed to return to room temperature and is added to 0.5 N NaOH (20 mL) in a separatory funnel and subsequently extracted with DCM (3×100 mL). The organic layers are combined, dried with $Na_2SO_4$, and concentrated. Purification by flash chromatography (0-6% MeOH in DCM) gave the product as a white solid (157 mg, 0.48 mmol, 63%). $^1$H NMR (400 MHz, Chloroform-d) δ 6.93 (b, 1H), 6.65-6.56 (m, 5H), 5.85 (b, 1H), 5.19 (s, 1H), 4.51 (s, 2H), 3.92 (s, 2H), 3.19 (sept, J=6.9, 1H), 2.24 (s, 6H), 1.23 (d, J=6.9 Hz, 6H). HRMS (ESI) m/z [M+Na+] $C_{20}H_{25}NNaO_3^+$ requires 350.1727, found 350.1737.

Example 8—N-(2,2-difluoroethyl)-2-(4-(4-hydroxy-3-isopropylbenzyl)-3,5-dimethylphenoxy)acetamide (Compound 6)

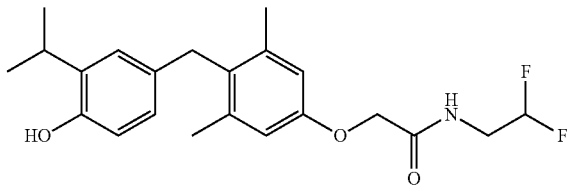 [SMILES: Cc1cc(OCC(=O)NCC(F)F)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Difluoroethylamine (87 mg, 1.075 mmol, 3 eq) is added as a solution in THF (0.2 mL). The reaction is stirred at room temperature for 1 h. The reaction solution is diluted with diethyl ether (20 mL) and washed with 0.5N HCl (2×20 mL) followed by brine (20 mL). The organic layer is dried with $Na_2SO_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of $BCl_3$ (1 M DCM, 0.72 mL, 2 eq) is added slowly and the reaction stirs for 15 min. The reaction is quenched with addition of a saturated $NaHCO_3$ solution (2 mL) and the flask is allowed to warm to room temperature. The reaction mixture is diluted with water (10 mL) and extracted with DCM (2×20 mL). The organic layers are combined, dried with $Na_2SO_4$, and concentrated under reduced pressure. Purification by flash chromatography (2-40% EtOAc in hexanes) gave the product as a clear, crystalline solid (79 mg, 0.2 mmol, 56%). $^1$H NMR (400 MHz, Chloroform-d) δ 6.94 (m, 2H), 6.65-6.55 (m, 4H), 5.91 (tt, J=55.8, 4.1 Hz, 1H), 5.19 (s, 1H), 4.55 (s, 2H), 3.93 (s, 2H), 3.77 (m, 2H), 3.20 (sept, J=6.9, 1H), 2.24 (s, 6H), 1.23 (d, J=6.9 Hz, 6H). HRMS (ESI) m/z [M+H+] $C_{22}H_{28}F_2NO_3^+$ requires=392.2032, found 392.2040.

Example 9—2-(4-(4-hydroxy-3-isopropylbenzyl)-3,5-dimethylphenoxy)-N-(2,2,2-trifluoroethyl)acetamide (Compound 7)

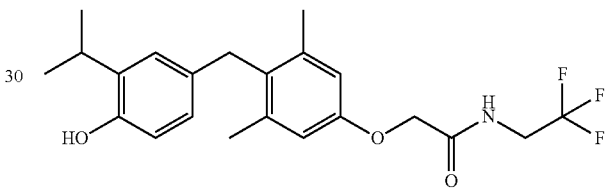

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq). Trifluoroethylamine hydrochloride (87 mg, 1.075 mmol, 3 eq) and DMAP (13 mg, 0.11 mmol, 0.3 eq) are added as a solution in THF (0.2 mL). The reaction is stirred at room temperature for 1 h. The reaction solution is diluted with diethyl ether (20 mL) and washed with 0.5N HCl (2×20 mL) followed by brine (20 mL). The organic layer is dried with $Na_2SO_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of $BCl_3$ (1M DCM, 0.72 mL, 2 eq) is added slowly and the reaction stirs for 15 min. The reaction is quenched with addition of a saturated $NaHCO_3$ solution (2 mL) and the flask is allowed to warm to room temperature. The reaction mixture is diluted with water (10 mL) and extracted with DCM (2×20 mL). The organic layers are combined, dried with $Na_2SO_4$, and concentrated under reduced pressure. Purification by flash chromatography (2-40% EtOAc in hexanes) gave the product as a white solid (89 mg, 0.22 mmol, 61%). $^1$H NMR (400 MHz, Chloroform-d) δ 6.93 (m, 2H), 6.65-6.57 (m, 4H), 4.80 (s, 1H), 4.58 (s, 2H), 4.05 (m, 2H), 3.93 (s, 2H), 3.18 (sept, J=6.8, 1H), 2.24 (s, 6H), 1.23 (d, J=6.8 Hz, 6H). HRMS (ESI) m/z [M+Na+] $C_{22}H_{26}F_3NNaO_3^+$ requires=432.1757, found 432.1762.

Example 10—2-(4-(4-hydroxy-3-isopropylbenzyl)-3,5-dimethylphenoxy)-N-methylacetamide (Compound 8)

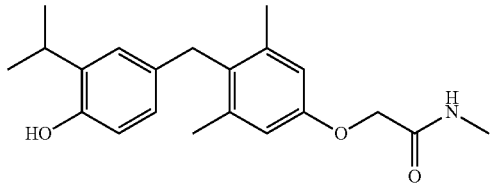 [SMILES: CNC(=O)COc1cc(C)c(Cc2ccc(O)c(C(C)C)c2)c(C)c1]

2-(4-(4-hydroxy-3-isopropylbenzyl)-3,5-dimethylphenoxy)acetic acid (GC-1, 155 mg, 0.47 mmol) was dissolved in 3 ml MeOH and 1 drop of sulfuric acid in a sealed tube. The sealed reaction mixture was then heated to 650 C with stirring for 1 hr. Upon cooling to room temperature, TLC of the mixture indicates complete conversion to the methyl ester intermediate. To the intermediate solution was then added 610 µL (7.05 mmol, 15 eq.) of 40% methyl amine in water and the reaction mixture was heated again to 65° C. for 1 hr in a sealed tube. The reaction is extracted from 200 mL of 0.5 N NaOH into 3×50 mL of DCM. The organic layers were combined, dried with $Na_2SO_4$, filtered and concentrated, then purified on silica (10% MeOH in DCM) to give the product as a white solid (144 mg, 90%). $^1$H NMR (400 MHz, CD3CN): 6.98 (br, 1H), 6.89 (s, 1H), 6.68 (s, 2H), 6.62 (d, 1H, J=8.6 Hz), 6.54 (dd, 1H, J=8.4, 2.4 Hz), 4.37 (s, 2H), 3.87 (s, 2H), 3.16 (septet, 1H, J=6.9 Hz), 2.75 (d, 3H, J=4.9 Hz), 2.20 (s, 6H), 1.12 (d, 6H, J=6.9 Hz). HRMS exact mass calcd for $C_{21}H_{27}NO_3$ [M+Na$^-$]$^+$: m/z 364.18831. Found m/z 364.18904.

Example 11—2-(4-(4-hydroxy-3-isopropyl benzyl)-3, 5-dimethylphenoxyl)-N-(2-hydroxyphenyl) acetamide (Compound 9)

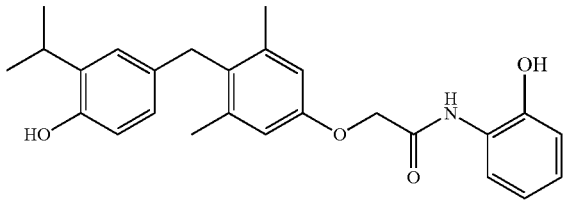 [SMILES: Cc1cc(OCC(=O)Nc2ccccc2O)cc(C)c1Cc1ccc(O)c(C(C)C)c1]

2-[4-(4-(benzyloxy)-3-isopropylbenzyl)-3, 5-dimethylphenoxy) acetic acid (250 mg, 0.6 mmol) was dissolved in 6 ml of dry DMF in a round bottom flask. 1-Ethyl-(3-dimethylaminopropyl) carbodiimide hydrochloride (EDC) (230 mg, 1.2 mmol), 1-Hydroxybenzotriazole (HOBt) (162 mg, 1.2 mmol) and diisopropylethylamine (DIEA) (418 uL, 2.4 mmol) were added to it and stirred for 1 hour at room temperature. 2-Aminophenol (130 mg, 1.2 mmol) was then added in one lot and the reaction mixture was stirred overnight at room temperature. Ethyl Acetate (15 ml) was then added and the reaction mixture was washed successively with 0.5 NHCl (2×5 ml), saturated $NaHCO_3$ solution (2×5 ml) and saturated NaCl solution (1×10 ml). It was then dried on anhydrous $MgSO_4$ and the solvent was removed in vacuo. The crude product was purified by Biotage flash chromatography, eluting with 10% to 40% ethyl acetate in hexane to obtain the pure benzyl protected GC-1 acetamide (154 mg, 0.3 mmol). 1H NMR (400 MHz, CDCl$_3$): δ 8.72 (s, 1H), 8.573 (s, 1H), 7.38-6.61 (m, 14H), 5.30 (s, 2H), 4.68 (s, 2H), 3.95 (s, 2H), 3.37 (m, 1H), 2.25 (s, 6H), 1.22 (d, J=6.57 Hz, 6H).

To a stirred suspension of this protected acetamide (150 mg, 0.29 mmol) and 10% Pd—C, wetted with ca. 55% water (60 mg) in 5 ml of methanol was added triethylsilane (441 uL, 2.9 mmol) dropwise under argon. The reaction mixture was stirred at room temperature for 2 hours. After completion of the reaction (TLC), it was filtered through celite and the solvent was removed in vacuo. The crude product was purified by Biotage flash chromatography, eluting with 10% to 40% ethyl acetate in hexane to obtain the final acetamide (79 mg, 0.18 mmol, 64% yield and 98.9% pure by HPLC). 1HNMR (400 MHz, CDCl$_3$): δ 8.70 (s, 1H), 8.57 (s, 1H), 7.16 (m, 1H), 7.08 (m, 1H), 6.92 (m, 2H), 6.72 (s, 2H), 6.59 (m, 2H), 4.68 (s, 2H), 3.93 (s, 2H), 3.13 (m, 1H), 2.26 (s, 6H), 1.22 (d, J=6.98 Hz, 6H). HRMS (M+Na) calcd for $C_{26}H_{29}NO_4$ 442.19888, found 442.19903.

Example 12—2-(4-(4-hydroxy-3-isopropyl benzyl)-N-(3-hydroxyphenyl) acetamide (Compound 10)

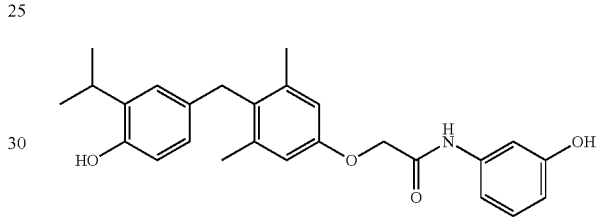

2-[4-(4-(benzyloxy)-3-isopropylbenzyl)-3, 5-dimethylphenoxy) acetic acid (250 mg, 0.6 mmol) is dissolved in 6 ml of dry DMF. 1-Ethyl-(3-dimethylaminopropyl) carbodiimide hydrochloride (EDC) (230 mg, 1.2 mmol), 1-Hydroxybenzotriazole (HOBt) (162 mg, 1.2 mmol) and diisopropylethylamine (DIEA) (418 uL, 2.4 mmol) were added to it and stirred for 1 hour at room temperature. To this solution was added 2-Aminophenol (130 mg, 1.2 mmol) in one lot and stirred overnight at room temperature. Ethyl Acetate (15 ml) was added to it and the reaction mixture was washed with 0.5 NHCl (2×10 ml), saturated $NaHCO_3$ solution (2×10 ml) and saturated NaCl solution (1×10 ml). It was then dried on anhydrous $MgSO_4$ and the solvent was removed in vacuo. The crude product was purified by Biotage flash chromatography, eluting with 10% to 40% ethyl acetate in hexane to obtain the pure benzyl protected GC-1 acetamide (186 mg, 0.36 mmol). 1H NMR (400 MHz, CDCl$_3$): δ 8.35 (s, 1H), 7.64 (s, 1H), 7.43-7.33 (m, 5H), 7.21-6.85 (m, 4H), 6.76-6.61 (m, 5H), 5.0 (s, 2H), 4.6 (s, 2H), 3.97 (s, 2H), 3.36 (m, 1H), 2.25 (s, 6H), 1.19 (d, J=6.94 Hz, 6H)

The protected acetamide (180 mg, 0.35 mmol) was dissolved in a mixture of methanol and THF (5 ml+6 ml) (11 ml) as it was not completely soluble in methanol only. 10% Pd—C, wetted with ca. 55% water (72 mg, 0.035 mmol) was added to it and triethylsilane (532 uL, 3.5 mmol) was added dropwise to the stirred suspension under argon. After completion of the reaction in 2 hours (TLC), the mixture was filtered through celite, and the solvent was removed in vacuo. The crude product was purified by Biotage flash chromatography, eluting with 20% to 60% ethyl acetate in hexane to obtain the final acetamide (75 mg, 0.17 mmol, 61% yield). 1HNMR (400 MHz, CDCl$_3$): δ 7.28 (m, 1H), 7.16 (t, J=7.89 Hz, 1H), 6.88 (m, 1H), 6.83 (m, 1H), 6.67 (s, 1H), 6.63 (m, 1H), 6.59 (d, J=7.89 Hz, 1H), 6.49 (m, 1H), 4.56 (s, 2H), 3.88 (s, 2H), 3.12 (m, 1H), 2.22 (s, 6H), 1.16 (d, J=6.85 Hz, 6H). HRMS (M+Na) calcd for C26H29NO4 442.19888, found 442.19939.

Example 13—2-(4-(4-hydroxy-3-isopropylbenzyl)-3,5-dimethylphenoxy)-N-(2-(methylsulfonamido)ethyl)acetamide (Compound 11)

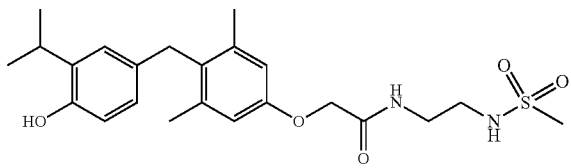 [SMILES: Cc1cc(OCC(=O)NCCNS(C)(=O)=O)cc(C)c1Cc1ccc(O)c(C(C)C)c1]

2-(4-(4-(benzyloxy)-3-isopropylbenzyl)-3,5-dimethylphenoxy)acetic acid (benzylated GC-1, 275 mg, 0.66 mmol) was dissolved in 1 mL of dry DMF. To this solution of the carboxylic acid was added DIEA (686 µL, 3.94 mmol), EDC HCl (253 mg, 1.31 mmol), and HOBt (178 mg, 1.31 mmol) and this solution was stirred for 1 hr at room temperature. The amine, N-(2-aminoethyl)methanesulfonamide (160 mg, 1.16 mmol) was then added and the reaction mixture stirred at room temperature for 18 hr. Dilution of the reaction mixture with 10 mL of EtOAc was followed by washing with 2×5 mL of 1 N HCl, 1× with 5 mL of saturated aqueous sodium bicarbonate, and 2× with 5 mL of brine. The resulting organic layer was dried with MgSO4, filtered, and concentrated to give the crude intermediate product (319 mg, 90%). The crude product was pure enough by $^1$H NMR to proceed without further purification.

The benzylated intermediate, 2-(4-(4-(benzyloxy)-3-isopropylbenzyl)-3,5-dimethylphenoxy)-N-(2-(methylsulfonamido)ethyl)acetamide (319 mg, 0.592 mmol), and pentamethylbenzene (292 mg, 1.97 mmol) was dissolved in 10 mL of dry DCM at −78° C. To this stirring solution at −78° C. was added BCl3 (3.3 ml, 3.3 mmol) and the reaction mixture was stirred for 2 hr before it was quenched with 10 mL of 9:1 CHCl3:MeOH and evaporated to a residue. This residue was washed with hexanes to afford a crude white solid which was purified chromatographically on silica (10% MeOH in DCM). The final product is an off-white solid (244 mg, 92%). $^1$H NMR (400 MHz, CD3CN): 7.29 (br, 1H), 6.89 (s, 1H), 6.69 (s, 2H), 6.62 (d, 1H, J=8.2 Hz), 6.54 (d, 1H, J=8.4, 2.0 Hz), 4.43 (s, 2H), 3.88 (s, 2H), 3.39 (m, 2H), 3.16 (m, 3H), 2.88 (s, 3H), 2.20 (s, 6H), 1.12 (d, 6H, J=6.9 Hz). HRMS exact mass calcd for $C_{23}H_{32}N_2O_5S$ [M+Na]$^+$: m/z 471.19241. Found m/z 471.19335.

Example 14—N-(1,3-dihydroxypropan-2-yl)-2-(4-(4-hydroxy-3-isopropylbenzyl)-3,5-dimethylphenoxy)acetamide (Compound 12)

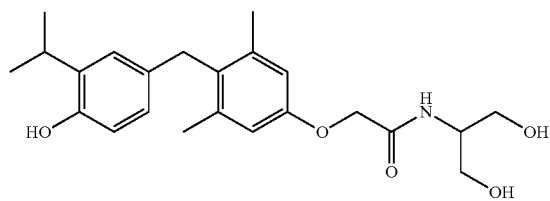 [SMILES: Cc1cc(OCC(=O)NC(CO)CO)cc(C)c1Cc1ccc(O)c(C(C)C)c1]

A stirring solution of GC-1 (411 mg, 1.25 mmol, 1 eq) is treated with DCM (6 mL) followed by addition of DCC (283 mg, 1.34 mmol, 1.1 eq) and N-hydroxysuccinimide (158 mg, 1.34 mmol, 1.1 eq). The reaction stirs for 4 h during which time a white precipitate forms. The urea byproduct is filitrered off and the intermediate NHS ester is purified by flash chromatography (0-80% EtOAc in hexanes) to give a white product (323 mg, 0.76 mol, 60%). The intermediate NHS ester (55 mg, 0.129 mmol, 1 eq) is treated with THF (1 mL) and triethylamine (27 µL, 0.19 mmol, 1.5 eq). The reaction is treated with (+/−)-serinol (17 mg, 0.19 mmol, 1.5 eq) and stirred for 30 min. The reaction mixture is purified directly by flash chromatography to give the product as a white solid (14 mg, 0.035 mmol, 27%). $^1$H NMR (400 MHz, Chloroform-d) δ 6.87 (s, 1H), 6.60-6.45 (m, 4H), 4.45 (s, 2H), 3.94 (m, 1H), 3.85 (s, 2H), 3.72-3.61 (m 2H), 3.19 (s, J=6.9 Hz, 1H), 2.65 (s, 1H), 2.24 (s, 6H), 1.23 (b, 8H). HRMS (ESI) m/z [M+Na+] $C_{23}H_{31}NNaO_5^+$ requires= 424.2094, found 424.2099.

Example 15—2-(4-(4-hydroxy-3-isopropylbenzyl)-3, 5-dimethylphenoxy)-N-propylacetamide (Compound 13)

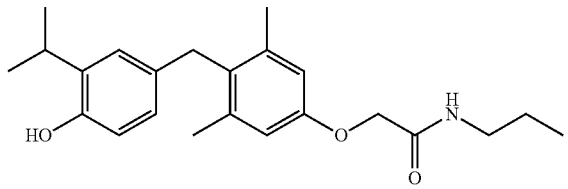 [SMILES: CCCNC(=O)COc1cc(C)c(Cc2ccc(O)c(C(C)C)c2)c(C)c1]

2-(4-(4-hydroxy-3-isopropylbenzyl)-3, 5-dimethylphenoxy) acetic acid (GC-1) (100 mg, 0.3 mmol) is dissolved in methanol in a sealed tube. Concentrated $H_2SO_4$ (1 drop) was added to it and it was heated at 65° C. Total conversion to the methyl ester was observed in 1 hour (TLC). Propyl amine (246 uL, 3 mmol) was added to it and then it was again heated at 65° C. for 1 hour. The reaction was not completed. So another 100 uL of propyl amine was added to it and the reaction went to completion in 30 minutes (TLC). It was cooled to 0° C. with ice water bath and 0.5N NaOH (10 ml) added to it and the reaction mixture was extracted with dichloromethane (3×50 ml). The organic layers were combined and dried on anhydrous MgSO4. The crude product was purified by Biotage flash chromatography eluting with 20% to 60% ethyl acetate and the pure propylacetamide was obtained (46 mg, 0.12 mmol, 41% yield and 99.3% pure by HPLC). 1HNMR (400 MHz, CDCl3): δ 6.91 (s, 1H), 6.63-6.53 (m, 5H), 4.48 (s, 2H), 3.90 (s, 2H), 3.31 (m, 2H), 3.15 (m, 1H), 2.22 (s, 6H), 1.59 (m, 2H), 1.21 (d, J=6.94 Hz, 6H), 0.94 (t, J=7.5 Hz, 3H). HRMS (M+Na) calcd for C23H31N03 392.21962, found 392.22036.

Example 16—N-(2-fluoroethyl)-2-(4-(4-hydroxy-3-isopropylbenzyl)-3,5-dimethylphenoxy)acetamide (Compound 14)

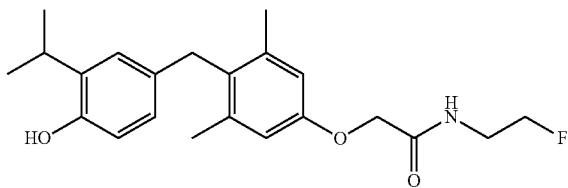 [SMILES: Cc1cc(OCC(=O)NCCF)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 150 mg, 0.36 mmol, 1 eq) is treated with dry THF (5 mL) and CDI (140 mg, 0.86 mmol, 2.4 eq) followed by heating to 45° C. for 2 h. The reaction is concentrated under reduced pressure and dissolved into THF (2.5 mL). The reaction solution is treated with 2-fluoroethylamine hydrochloride (87 mg, 1.075 mmol, 3 eq) and stirred at room temperature for 1 h. The reaction solution is diluted with diethyl ether (20 mL) and washed with 0.5N HCl (2×20 mL) followed by brine (20 mL). The organic layer is dried with Na$_2$SO$_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of BCl$_3$ (1 M DCM, 0.72 mL, 2 eq) is added slowly and the reaction stirs for 15 min. The reaction is quenched with addition of a saturated NaHCO$_3$ solution (2 mL) and the flask is allowed to warm to room temperature. The reaction mixture is diluted with water (10 mL) and extracted with DCM (2×20 mL). The organic layers are combined, dried with Na$_2$SO$_4$, and concentrated under reduced pressure. Purification by flash chromatography (2-40% EtOAc in hexanes) gave the product as a white solid (70 mg, 0.19 mmol, 52%). $^1$H NMR (400 MHz, Chloroform-d) δ 7.03 (s, 1H), 6.94 (d, J=2.1 Hz, 1H), 6.68-6.52 (m, 4H), 4.76 (s, 1H), 4.62 (dt, J=47.4, 4.8 Hz, 1H), 4.53 (s, 2H), 3.93 (s, 2H), 3.71 (dq, J=27.8, 5.0 Hz, 2H), 3.17 (hept, J=7.0 Hz, 1H), 2.24 (s, 6H), 1.23 (d, J=6.9 Hz, 6H).

Example 17—N-allyl-2-(4-(4-hydroxy-3-isopropylbenzyl)-3,5-dimethylphenoxy)acetamide (Compound 15)

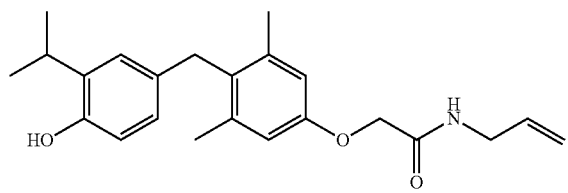 [SMILES: C=CCNC(=O)COc1cc(C)c(Cc2ccc(O)c(C(C)C)c2)c(C)c1]

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Allylamine hydrochloride (90 mg, 1.075 mmol, 3 eq) is added to the reaction solution, which is stirred at room temperature overnight. The reaction solution is diluted with diethyl ether (20 mL) and washed with 0.5N HCl (2×20 mL) followed by brine (20 mL). The organic layer is dried with Na$_2$SO$_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of BCl$_3$ (1 M DCM, 0.72 mL, 2 eq) is added slowly and the reaction stirs for 15 min. The reaction is quenched with addition of a saturated NaHCO$_3$ solution (2 mL) and the flask is allowed to warm to room temperature. The reaction mixture is diluted with water (10 mL) and extracted with DCM (2×20 mL). The organic layers are combined, dried with Na$_2$SO$_4$, and concentrated under reduced pressure. Purification by flash chromatography (2-40% EtOAc in hexanes) gave the product as a white solid (70 mg, 0.2 mmol, 55%). $^1$H NMR (400 MHz, Chloroform-d) δ 6.94 (d, J=2.1 Hz, 1H), 6.75 (s, 1H), 6.68-6.52 (m, 4H), 5.96-5.81 (m, 1H), 5.27-5.14 (m, 2H), 4.96 (s, 1H), 4.54 (s, 2H), 4.02 (tt, J=5.8, 1.6 Hz, 2H), 3.93 (s, 2H), 3.19 (hept, J=6.9 Hz, 1H), 2.24 (s, 6H), 1.23 (d, J=6.9 Hz, 6H).

Example 18—2-(4-(4-hydroxy-3-isopropylbenzyl)-3,5-dimethylphenoxy)-N-(prop-2-yn-1-yl)acetamide (Compound 16)

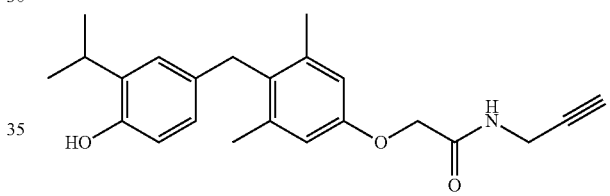

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Propargylamine (90 mg, 1.075 mmol, 3 eq) is added to the reaction solution as a solution in THF (0.2 mL). The reaction stirs at room temperature for 1 h. The reaction solution is diluted with diethyl ether (20 mL) and washed with 0.5N HCl (2×20 mL) followed by brine (20 mL). The organic layer is dried with Na$_2$SO$_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of BCl$_3$ (1 M DCM, 0.72 mL, 2 eq) is added slowly and the reaction stirs for 15 min. The reaction is quenched with addition of a saturated NaHCO$_3$ solution (2 mL) and the flask is allowed to warm to room temperature. The reaction mixture is diluted with water (10 mL) and extracted with DCM (2×20 mL). The organic layers are combined, dried with Na$_2$SO$_4$, and concentrated under reduced pressure. Purification by flash chromatography (2-40% EtOAc in hexanes) gave the product as an off-white solid (88 mg, 0.24 mmol, 67%). $^1$H NMR (400 MHz, Chloroform-d) δ 6.92 (t, J=3.5 Hz, 2H), 6.63 (d, J=8.1 Hz, 1H), 6.63 (s, 2H), 6.53 (dd, J=8.2, 2.2 Hz, 1H), 5.69 (s, 1H), 4.51 (s, 2H), 4.16 (dd, J=5.5, 2.6 Hz, 2H), 3.90 (s, 2H), 3.20 (hept, J=6.9 Hz, 1H), 2.22 (s, 6H), 1.21 (d, J=6.9 Hz, 6H).

Example 19—2-(4-(4-hydroxy-3-isopropylbenzyl)-3,5-dimethylphenoxy)-N-methoxyacetamide (Compound 17)

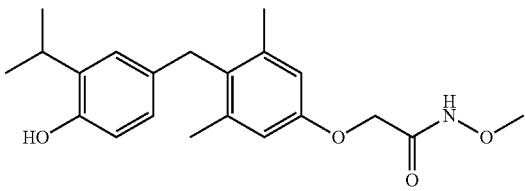 [SMILES: CONC(=O)COc1cc(C)c(Cc2ccc(O)c(C(C)C)c2)c(C)c1]

A stirring solution of 2-(4-(4-(benzyloxy)-3-isopropyl-benzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Methoxylamine hydrochloride (83 mg, 1.075 mmol, 3 eq) is added to the reaction solution, which is stirred at room temperature overnight. The reaction solution is diluted with diethyl ether (20 mL) and washed with 0.5N HCl (2×20 mL) followed by brine (20 mL). The organic layer is dried with $Na_2SO_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of $BCl_3$ (1 M DCM, 0.72 mL, 2 eq) is added slowly and the reaction stirs for 15 min. The reaction is quenched with addition of a saturated $NaHCO_3$ solution (2 mL) and the flask is allowed to warm to room temperature. The reaction mixture is diluted with water (10 mL) and extracted with DCM (2×20 mL). The organic layers are combined, dried with $Na_2SO_4$, and concentrated under reduced pressure. Purification by flash chromatography (2-40% EtOAc in hexanes) gave the product as a white solid (94.5 mg, 0.26 mmol, 72%). $^1$H NMR (400 MHz, Chloroform-d) δ 9.06 (s, 1H), 6.93 (d, J=2.1 Hz, 1H), 6.66-6.52 (m, 4H), 4.74 (s, 1H), 4.59 (s, 2H), 3.92 (s, 2H), 3.86 (s, 3H), 3.18 (hept, J=6.9 Hz, 1H), 2.24 (s, 6H), 1.23 (d, J=6.9 Hz, 6H).

Example 20—N-(3,4-dihydroxyphenethyl)-2-(4-(4-hydroxy-3-isopropylbenzyl)-3,5-dimethylphenoxy)acetamide (Compound 18)

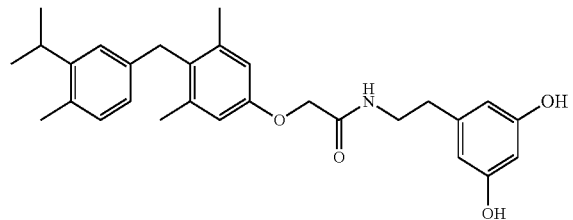 [SMILES: Cc1ccc(Cc2c(C)cc(OCC(=O)NCCc3cc(O)cc(O)c3)cc2C)cc1C(C)C]

2-[4-(4-(benzyloxy)-3-isopropylbenzyl)-3, 5-dimethylphenoxy) acetic acid (200 mg, 0.48 mmol) was dissolved in 10 ml of dry THF in a round bottom flask. 1,1'-Carbonyl diimidazole (CDI) (78 mg, 0.48 mmol), was added to it and stirred at 45° C. for 3 hours. The reaction was monitored by TLC and when complete conversion to the acylimidazolide was observed, the mixture was concentrated to dryness in vacuo to remove all $CO_2$. This was then dissolved in dry THF (8 mL) and a solution of dopamine hydrochloride (118.33 mg, 0.624 mmol, 1.3 eq) in 2 ml of dry MeOH was slowly added to it. The reaction mixture was stirred overnight at 45° C. It was then cooled and the solvent evaporated in vacuo. Ethyl Acetate (25 mL) was added to it and the reaction mixture was washed successively with 0.5N HCl (2×5 mL) and saturated NaCl solution (1×10 mL). It was dried on anhydrous $MgSO_4$ and the solvent was removed in vacuo. The crude product was purified by Biotage flash chromatography, eluting with 10% to 40% ethyl acetate in hexane. The benzyl protected GC-1 acetamide was crystallized from chloroform (100 mg, 0.17 mmol). $^1$H NMR (400 MHz, Methanol-d4): δ 7.48-7.26 (m, 3H), 6.93 (d, J=2.3 Hz, 1H), 6.82 (dd, J=8.5, 1.3 Hz, 1H), 6.71-6.62 (m, 3H), 6.51 (dd, J=8.1, 2.0 Hz, 1H), 5.03 (s, 1H), 4.47 (d, J=1.4 Hz, 1H), 3.95 (s, 1H), 3.45 (dd, J=8.1, 6.7 Hz, 1H), 3.38-3.26 (m, 1H), 2.67 (t, J=7.4 Hz, 1H), 2.22 (s, 3H), 1.16 (dd, J=6.9, 1.3 Hz, 3H).

To a stirred solution of this protected acetamide (75 mg, 0.13 mmol) and 10% Pd—C wetted with ca. 55% water (27.6 mg) in 5 mL of methanol was added triethylsilane (198 μL, 1.3 mmol) dropwise under argon. The reaction mixture was stirred at room temperature for 3 hours. After completion of the reaction (TLC), it was filtered through celite and the solvent was removed in vacuo. The crude product was purified by Biotage flash chromatography, eluting with 30% to 80% dichloromethane in ethyl acetate to obtain the final acetamide (42 mg, 0.18 mmol, 67% yield and 99% pure by HPLC). $^1$H NMR (400 MHz, $CDCl_3$): δ 6.84 (d, J=2.1 Hz, 1H), 6.69 (d, J=6.8 Hz, 4H), 6.63-6.49 (m, 3H), 4.48 (s, 2H), 3.92 (s, 2H), 3.47 (t, J=7.4 Hz, 2H), 3.22 (hept, J=6.9 Hz, 1H), 2.69 (t, J=7.4 Hz, 2H), 2.23 (s, 6H), 1.32 (s, 1H), 1.15 (d, J=6.9 Hz, 6H), 0.93 (t, J=7.0 Hz, 2H).

Example 21—2-(4-(4-hydroxy-3-isopropylbenzyl)-3, 5-dimethylphenoxy)-N-phenethylacetamide (Compound 19)

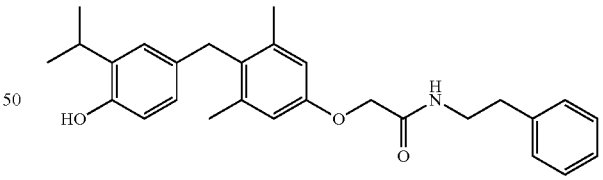

2-[4-(4-(benzyloxy)-3-isopropylbenzyl)-3, 5-dimethylphenoxy) acetic acid (200 mg, 0.48 mmol) was dissolved in 10 ml of dry THF in a round bottom flask. 1,1'-Carbonyl diimidazole (78 mg, 0.48 mmol), was added to it and stirred at 45° C. for 3 hours. The reaction was monitored by TLC and when complete conversion to the acylimidazolide was observed, the mixture was concentrated to dryness in vacuo to remove all $CO_2$. This was then dissolved in dry THF (8 mL) and a solution 2-phenylethylamine (157.5 mg, 1.44 mmol, 1.33 eq) in 2 mL of dry THF was added to it dropwise. The reaction mixture was stirred at 45° C. overnight. It was then cooled and the solvent evaporated in vacuo. It was dissolved in ethyl acetate (25 mL) and washed successively with 0.5N HCl (2×5 mL) and saturated NaCl solution (1×10 mL). It was then dried on anhydrous MgSO$_4$ and the solvent was removed in vacuo. The crude product was purified by Biotage flash chromatography, eluting with 10% to 40% ethyl acetate in hexane. $^1$H NMR (400 MHz, Chloroform-d) δ 7.46-7.14 (m, 11H), 6.98 (d, J=2.1 Hz, 1H), 6.73 (dd, J=8.4, 1.2 Hz, 1H), 6.70-6.55 (m, 4H), 5.02 (s, 2H), 4.47 (s, 2H), 3.93 (s, 2H), 3.66-3.56 (m, 2H), 3.35 (hept, J=6.9 Hz, 1H), 2.85 (t, J=7.0 Hz, 2H), 2.23 (s, 6H), 1.20 (dd, J=7.0, 1.2 Hz, 6H).

The deprotection of the benzyl group of the acetamide thus prepared was done with BCl$_3$. The acetamide (220 mg, 0.42 mmol) is dissolved in dry dichloromethane (10 mL) and pentamethyl benzene (125 mg, 0.84 mmol) added to it. The solution was then cooled to −78° C. using a dry ice/acetone bath and 1 ml of 1 M solution of BCl$_3$ in dichloromethane (117 mg, 1 mmol) was added to it very slowly. It was stirred at −78° C. for 20 mins and total conversion to the product was observed by TLC. Saturated sodium bicarbonate solution (5 mL) was then added at −78° C. The reaction mixture was warmed up at room temperature. Dichloromethane (25 mL) and water (5 mL) was then added to it and the organic layer was collected. The aqueous layer was extracted with dichloromethane (2×10 mL) and the combined organic layer was dried on anhydrous magnesium sulfate. The crude product was purified by Biotage flash chromatography, eluting with 20% to 60% ethyl acetate in hexane to obtain the final acetamide (134 mg, 0.31 mmol, 74% yield and 99.6% pure by HPLC). $^1$H NMR (400 MHz, CDCl$_3$): δ 7.34-7.12 (m, 5H), 6.92 (d, J=2.1 Hz, 1H), 6.67 (s, 1H), 6.62-6.50 (m, 4H), 4.67 (s, 1H), 4.46 (s, 2H), 3.90 (s, 2H), 3.61 (q, J=6.8 Hz, 2H), 3.15 (hept, J=6.9 Hz, 1H), 2.84 (t, J=7.0 Hz, 2H), 2.22 (5, 6H), 1.21 (d, J=6.9 Hz, 6H).

Example 22—N-hydroxy-2-(4-(4-hydroxy-3-isopropylbenzyl)-3,5-dimethylphenoxy)acetamide (Compound 20)

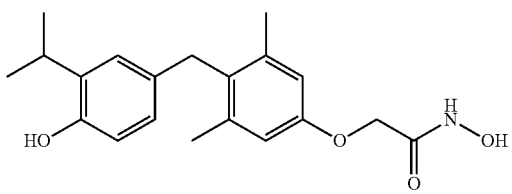 [SMILES: Cc1cc(OCC(=O)NO)cc(C)c1Cc1ccc(O)c(C(C)C)c1]

2-(4-(4-(benzyloxy)-3-isopropylbenzyl)-3,5-dimethylphenoxy)acetic acid (benzylated GC-1, 150 mg, 0.36 mmol) was dissolved in 6 mL of dry THF. To this solution of the carboxylic acid was added 1,1'-carbonyldiimidazole (70 mg, 0.43 mmol) under argon and this solution was stirred for 2 hr at 50° C. Hydroxylamine hydrochloride (30 mg, 0.43 mmol) in 3 mL MeOH was then added and the reaction mixture stirred at 50° C. for 18 hr. The reaction mixture was then evaporated to dryness in vacuo, dissolved in 10 mL DCM and washed with 2×5 mL of 1 N HCl and 2× with 5 mL of brine. The resulting organic layer was dried with MgSO$_4$, filtered, and concentrated to give the crude intermediate product (139 mg, 90%). The crude product was pure enough by $^1$H NMR to proceed without further purification.

The benzylated intermediate, 2-(4-(4-(benzyloxy)-3-isopropylbenzyl)-3,5-dimethylphenoxy)-N-hydroxyacetamide (139 mg, 0.321 mmol), and pentamethylbenzene (160 mg, 1.07 mmol) was dissolved in 10 mL of dry DCM at −78° C. To this stirring solution at −78° C. was added BCl$_3$ (1.1 ml, 1.1 mmol) and the reaction mixture was stirred for 2 hr before it was quenched with 10 mL of 9:1 CHCl$_3$:MeOH and evaporated to a residue. This residue was washed with hexanes to afford a crude white solid which was purified chromatographically on silica (10% MeOH in DCM). The final product is an off-white solid (51 mg, 46%). The product tests positive (red-orange stain) with iron (III) chloride on TLC. $^1$H NMR (400 MHz, MeOD): 6.78 (s, 1H), 6.65 (s, 2H), 6.54 (d, 1H, J=8.3 Hz), 6.48 (dd, 1H, J=8.3, 2 Hz), 4.48 (s, 2H), 3.85 (s, 2H), 3.15 (sept. 1H), 2.16 (s, 6H), 1.08 (d, 6H, J=6.9 Hz).

Example 23—2-(4-(4-hydroxy-3-isopropylbenzyl)-3,5-dimethylphenoxy)acetohydrazide (Compound 21)

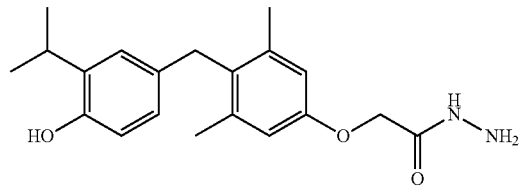 [SMILES: Cc1cc(OCC(=O)NN)cc(C)c1Cc1ccc(O)c(C(C)C)c1]

2-(4-(4-hydroxy-3-isopropylbenzyl)-3,5-dimethylphenoxy)acetic acid (sobetirome, 50 mg, 0.15 mmol) was dissolved in 3 ml MeOH and 1 drop of sulfuric acid in a sealed tube. The sealed reaction mixture was then heated to 65° C. with stirring for 1 hr. Upon cooling to room temperature, TLC of the mixture indicates complete conversion to the methyl ester intermediate. To the intermediate solution was then added 44 μL (0.9 mmol, 6 eq.) of hydrazine monohydrate and the reaction mixture was stirred for 1 hr in a sealed tube. The reaction was extracted from 50 mL of water into 3×20 mL of DCM. The organic layers were combined, dried with Na$_2$SO$_4$, filtered and concentrated, then purified on silica (10% MeOH in DCM) to give the product as a white solid (44 mg, 86%). The product tests positive with ninhydrin on TLC. $^1$H NMR (400 MHz, MeOD): 6.77 (s, 1H), 6.64 (s, 2H), 6.53 (d, 1H, J=8.2 Hz), 6.46 (dd, 1H, J=8.3, 2 Hz), 4.48 (s, 2H), 3.83 (s, 2H), 3.16 (sept. 1H), 2.16 (s, 6H), 1.08 (d, 6H, J=6.9 Hz.

Example 25—Sodium 2-(2-(4-(4-hydroxy-3-isopropylbenzyl)-3,5-dimethylphenoxy)acetamido)ethane-1-sulfonate (Compound 23)

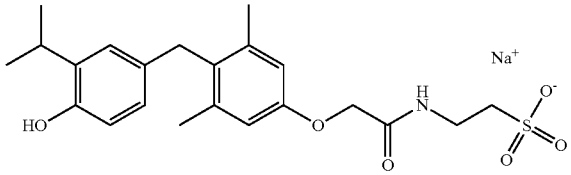 [SMILES: Cc1cc(OCC(=O)NCCS(=O)(=O)[O-])cc(C)c1Cc1ccc(O)c(C(C)C)c1 ; [Na+]]

GC-1 (100 mg, 0.3 mmol, 1 eq) is treated with MeOH (5 mL) in a sealed tube. Sulfuric acid (1 drop) is added and the reaction is sealed and then heated to 65° C. for 1 hour while stirring. The reaction is allowed to come to room temperature. TLC analysis (1:30 MeOH:DCM) shows complete conversion to the intermediate methyl ester. To the intermediate reaction mixture, taurine (229 mg, 1.83 mmol, 6 eq) is added as a solution with sodium hydroxide (73 mg, 1.83 mmol, 6 eq) in water (2 mL). The reaction is resealed and, again, heated to 65° C. overnight. A portion of the solvent is removed under reduced pressure and the total volume of the solution is adjusted to ~5 mL with additional water. The solution is filtered through a 0.22 μm filter and purified by preparative HPLC. The combined product fractions were combined and concentrated by a steady stream of air followed by reduced pressure to give a white solid (7.8 mg, 0.02 mmol, 5%). $^1$H NMR (400 MHz, 9:1 Chloroform-d: Methanol-d4) δ 6.85 (d, J=2.2 Hz, 1H), 6.61-6.52 (m, 3H), 6.43 (dd, J=8.2, 2.3 Hz, 1H), 4.40 (s, 2H), 3.83 (s, 2H), 3.72 (t, J=6.0 Hz, 2H), 3.37 (s, 6H), 3.17 (hept, J=6.9 Hz, 1H), 3.02 (t, J=6.0 Hz, 2H), 2.15 (s, 6H), 1.13 (d, J=6.9 Hz, 6H).

Example 26—N-cyclopropyl-2-(4-(4-hydroxy-3-isopropylbenzyl)-3,5-dimethylphenoxy)acetamide (Compound 24)

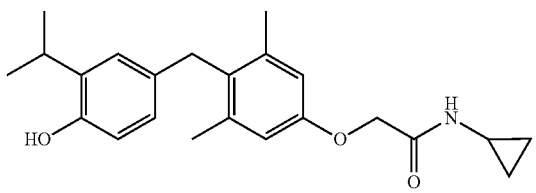 [SMILES: Cc1cc(OCC(=O)NC2CC2)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Cyclopropylamine (60 mg, 1.075 mmol, 3 eq) is added to the reaction solution, which is stirred at room temperature overnight. The reaction solution is diluted with diethyl ether (20 mL) and washed with 0.5N HCl (2×20 mL) followed by brine (20 mL). The organic layer is dried with Na$_2$SO$_4$ and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of BCl$_3$ (1 M DCM, 0.72 mL, 2 eq) is added slowly and the reaction stirs for 15 min. The reaction is quenched with addition of a saturated NaHCO$_3$ solution (2 mL) and the flask is allowed to warm to room temperature. The reaction mixture is diluted with water (10 mL) and extracted with DCM (2×20 mL). The organic layers are combined, dried with Na$_2$SO$_4$, and concentrated under reduced pressure. Purification by flash chromatography (2-40% EtOAc in hexanes) gave the product as a white solid (63 mg, 0.17 mmol, 48%). $^1$H NMR (400 MHz, Chloroform-d) δ 6.93 (d, J=2.1 Hz, 1H), 6.76 (s, 1H), 6.67 (d, J=8.1 Hz, 1H), 6.62 (s, 2H), 6.54 (dd, J=8.2, 2.2 Hz, 1H), 5.94 (s, 1H), 4.48 (s, 2H), 3.92 (s, 2H), 3.23 (hept, J=6.9 Hz, 1H), 2.82 (tq, J=7.2, 3.7 Hz, 1H), 2.23 (s, 6H), 1.23 (d, J=6.9 Hz, 6H), 0.95-0.80 (m, 2H), 0.71-0.56 (m, 2H).

Example 27—2-(4-(4-hydroxy-3-isopropylbenzyl)-3,5-dimethylphenoxy)-N,N-dimethylacetamide

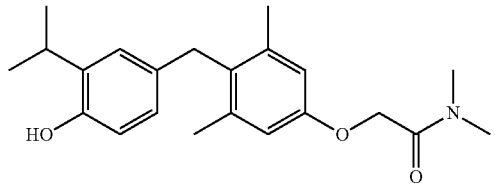 [SMILES: Cc1cc(OCC(=O)N(C)C)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 300 mg, 0.72 mmol, 2 eq) is treated with dry THF (5 mL) and CDI (140 mg, 0.86 mmol, 2.4 eq) followed by heating to 45° C. for 2 h. The reaction is concentrated under reduced pressure and dissolved into THF (5 mL). Half of the reaction is taken onto the next step (0.36 mmol, 1 eq) and is treated with THF (2.5 mL). Dimethylamine hydrochloride (88 mg, 1.075 mmol, 3 eq) is added to the reaction solution, which is stirred at room temperature overnight. The reaction solution is diluted with diethyl ether (20 mL) and washed with 0.5N HCl (2×20 mL) followed by brine (20 mL). The organic layer is dried with Na2SO4 and concentration under reduced pressure. The crude intermediate is taken up in DCM (3 mL) and placed under argon. Pentamethylbenzene (106 mg, 0.72 mmol, 2 eq) is added and the reaction is cooled to −78° C. A solution of BCl3 (1 M DCM, 0.72 mL, 2 eq) is added slowly and the reaction stirs for 15 min. The reaction is quenched with addition of a saturated NaHCO$_3$ solution (2 mL) and the flask is allowed to warm to room temperature. The reaction mixture is diluted with water (10 mL) and extracted with DCM (2×20 mL). The organic layers are combined, dried with Na2SO4, and concentrated under reduced pressure. Purification by flash chromatography (2-40% EtOAc in hexanes) gave the product as a white solid (38 mg, 0.11 mmol, 30%). 1H NMR (400 MHz, Chloroform-d) δ 6.95 (d, J=2.1 Hz, 1H), 6.65 (d, J=9.9 Hz, 3H), 6.53 (dd, J=8.2, 2.2 Hz, 1H), 5.58 (s, 1H), 4.68 (s, 2H), 3.90 (s, 2H), 3.21 (h, J=6.9 Hz, 1H), 3.13 (s, 3H), 3.02 (s, 3H), 2.20 (s, 6H), 1.23 (d, J=6.8 Hz, 6H).

Example 28—N-ethyl-2-(4-(4-hydroxy-3-isopropylbenzyl)-3,5-dimethylphenoxy)acetamide

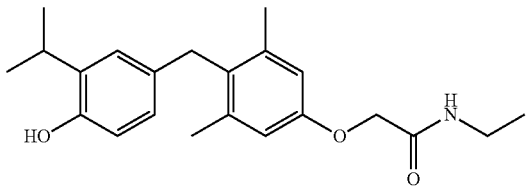

GC-1 (100 mg, 0.304 mmol, 1 eq) is treated with MeOH (3 mL) in a sealed tube. Sulfuric acid (1 drop) is added and the reaction is sealed and then heated to 65° C. for 1 hour while stirring. The reaction is allowed to come to room temperature. TLC analysis (1:30 MeOH:DCM) shows complete conversion to the intermediate methyl ester. To the intermediate reaction mixture, ethylamine (33% in water, 0.25 mL, 1.84 mmol, 6 eq) is added. The reaction is resealed and, again, heated to 65° C. for 1 hour. The reaction flask is allowed to return to room temperature and is added to 0.5 N NaOH (20 mL) in a separatory funnel and subsequently extracted with DCM (3×100 mL). The organic layers are combined, dried with $Na_2SO_4$, and concentrated. Purification by flash chromatography (0-6% MeOH in DCM) gave the product as a white solid (82 mg, 0.23 mmol, 76%). $^1$H NMR (400 MHz, Chloroform-d) δ 6.94 (d, J=2.2 Hz, 1H), 6.72-6.61 (m, 4H), 6.55 (dd, J=8.1, 2.2 Hz, 1H), 5.77 (d, J=17.7 Hz, 1H), 4.50 (s, 2H), 3.92 (s, 2H), 3.43 (qd, J=7.3, 5.8 Hz, 2H), 3.22 (hept, J=6.8 Hz, 1H), 2.24 (s, 6H), 1.32-1.15 (m, 9H).

Example 29—N-(cyanomethyl)-2-(4-(4-hydroxy-3-isopropylbenzyl)-3, 5-dimethylphenoxy)acetamide (Compound 27)

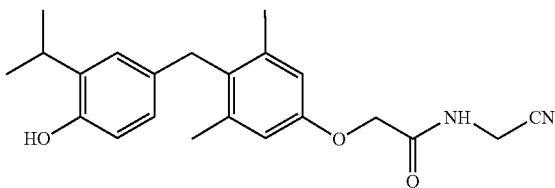 [SMILES: Cc1cc(OCC(=O)NCC#N)cc(C)c1Cc1ccc(O)c(C(C)C)c1]

2-[4-(4-(benzyloxy)-3-isopropylbenzyl)-3, 5-dimethylphenoxy) acetic acid (200 mg, 0.48 mmol) was dissolved in 10 mL of dry THF in a flame dried round bottom flask. 1,1'-Carbonyl diimidazole (85 mg, 0.52 mmol, 1.1 eq), was added to it and stirred at 45° C. for 3 hours. The reaction was monitored by TLC and when complete conversion to the acylimidazolide was observed, the mixture was concentrated to dryness in vacuo to remove all $CO_2$. This was then dissolved in dry THF (8 mL) and amino acetonitrile hydrochloride (133 mg, 1.44 mmol, 3 eq) was added to it in one portion. The reaction mixture was stirred at 45° C. overnight. White solid precipitated out from the reaction mixture. It was cooled and THF was removed in vacuo. The solid was dissolved ethyl acetate (25 mL) and the reaction mixture was washed successively with 0.5N HCl (2×5 mL) and saturated NaCl solution (1×10 mL). It was then dried on anhydrous $MgSO_4$ and the solvent was removed in vacuo. The resulting mixture solidified on keeping in the refrigerator. It was washed with hexane and the NMR showed it to be more than 90% pure. 1 HNMR (400 MHz, Methanol-d4) δ 7.50-7.27 (m, 5H), 6.94 (d, J=2.3 Hz, 1H), 6.85 (d, J=8.3 Hz, 1H), 6.74 (s, 2H), 6.69 (dd, J=8.4, 2.3 Hz, 1H), 5.06 (s, 2H), 4.59 (s, 1H), 4.27 (s, 2H), 3.96 (s, 2H), 2.31 (s, 1H), 2.24 (s, 6H), 1.18 (dd, J=6.9, 1.5 Hz, 6H), 0.95 (d, J=6.7 Hz, 1H).

The benzyl protected group was cleaved by $BCl_3$. The acetamide (175 mg, 0.38 mmol) was dissolved in dry dichloromethane (10 ml) and pentamethyl benzene (113 mg, 0.76 mmol) was added to it. The solution was then cooled to −78° C. using a dry ice/acetone bath and 1 M solution of $BCl_3$ in dichloromethane (789 uL, 89 mg, 0.76 mmol) was added to it very slowly. TLC showed major conversion to the product in 25 minutes of stirring at −78° C. Saturated sodium bi-carbonate solution (5 ml) was then added to it at −78° C. The reaction mixture was warmed up at room temperature. Dichloromethane (25 ml) and water (5 ml) was then added to it and the organic layer was collected. The aqueous layer was extracted with dichloromethane (2×10 ml) and the combined organic layer was dried on anhydrous magnesium sulfate. The crude product was purified by Biotage flash chromatography, eluting with 10% to 50% ethyl acetate in hexane to obtain the final acetamide (85 mg, 0.23 mmol, 60% yield and 99.6% pure by HPLC). $^1$H NMR (400 MHz, Methanol-d4) δ 6.83 (d, J=2.2 Hz, 1H), 6.72 (s, 2H), 6.62-6.49 (m, 2H), 4.57 (d, J=1.6 Hz, 2H), 4.25 (d, J=1.6 Hz, 2H), 3.90 (s, 2H), 3.21 (hept, 1H), 2.22 (d, J=1.5 Hz, 6H), 1.14 (dd, J=7.0, 1.7 Hz, 6H).

Example 30—N-(3-fluorophenyl)-2-(4-(4-hydroxy-3-isopropylbenzyl)-3,5-dimethylphenoxy)acetamide (Compound 28)

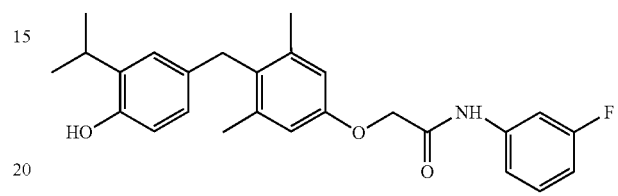

2-[4-(4-(benzyloxy)-3-isopropylbenzyl)-3, 5-dimethylphenoxy) acetic acid (200 mg, 0.48 mmol) was dissolved in 10 mL of dry THF in a round bottom flask. 1,1'-Carbonyl diimidazole (78 mg, 0.48 mmol), was added to it and stirred at 45° C. for 3 hours. The reaction was monitored by TLC and when complete conversion to the acylimidazoleide was observed, the mixture was concentrated to dryness in vacuo to remove all $CO_2$. This was then dissolved in dry THF (8 mL) and a solution 3-fluoroaniline (144.4 mg, 1.44 mmol, 1.33 eq) in 2 mL of dry THF was added to it dropwise. The reaction mixture was then stirred at 45° C. overnight. The reaction mixture was cooled and the solvent evaporated in vacuo. Ethyl acetate (25 mL) was then added and the reaction mixture was washed successively with 0.5N HCl (2×5 mL) and saturated NaCl solution (1×10 mL). It was then dried on anhydrous $MgSO_4$ and the solvent was removed in vacuo. The crude product was purified by Biotage flash chromatography, eluting with 10% to 40% ethyl acetate in hexane. 1H NMR (400 MHz, chloroform-d) δ 8.34 (s, 1H), 7.56 (dt, J=10.7, 2.3 Hz, 1H), 7.44-7.18 (m, 7H), 6.95 (d, J=2.3 Hz, 1H), 6.84 (tdd, J=8.2, 2.5, 1.1 Hz, 1H), 6.73 (d, J=8.4 Hz, 1H), 6.68 (s, 2H), 6.60 (dd, J=8.4, 2.3 Hz, 1H), 5.00 (s, 2H), 4.59 (s, 2H), 3.92 (s, 2H), 3.34 (hept, J=6.9 Hz, 1H), 2.23 (s, 6H), 1.18 (d, J=6.9 Hz, 6H).

The acetamide (200 mg, 0.39 mmol) was dissolved in dry dichloromethane (10 ml) and pentamethyl benzene (116 mg, 0.78 mmol) was added to it. The solution was then cooled to −78° C. using a dry ice/acetone bath and 1 M solution of $BCl_3$ in dichloromethane (777 μL, 91 mg, 0.78 mmol) was added to it very slowly. TLC showed total conversion to the product within 15 minutes of stirring at −78° C. Saturated sodium bi-carbonate solution (5 mL) was then added to it at −78° C. The reaction mixture was then warmed up at room temperature. Dichloromethane (25 mL) and water (5 mL) was then added to it and the organic layer was collected. The aqueous layer was extracted with dichloromethane (2×10 mL) and the combined organic layer was dried on anhydrous magnesium sulfate. The crude product was purified by Biotage flash chromatography, eluting with 10% to 50% ethyl acetate in hexane to obtain the final acetamide (150 mg, 0.35 mmol, 91% yield and 96.8% pure by HPLC). 1H NMR (400 MHz, chloroform-d) δ 8.34 (s, 1H), 7.34-7.17 (m, 2H), 6.92-6.79 (m, 2H), 6.68 (s, 2H), 6.61-6.49 (m, 2H), 4.58 (s, 3H), 3.90 (s, 2H), 3.13 (hept, J=6.8 Hz, 1H), 1.19 (d, J=6.9 Hz, 6H).

Example 31—2-(4-(4-hydroxy-3-isopropylbenzyl)-
3,5-dimethylphenoxy)-N-(oxetan-3-yl)acetamide
(Compound 29)

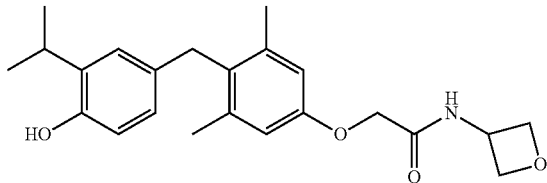 [SMILES: Cc1cc(OCC(=O)NC2COC2)cc(C)c1Cc1ccc(O)c(C(C)C)c1]

2-(4-(4-(benzyloxy)-3-isopropylbenzyl)-3,5-dimethylphenoxy)acetic acid (benzylated GC-1, 200 mg, 0.48 mmol) was dissolved in 6 mL of dry THF. To this solution of the carboxylic acid was added 1,1'-carbonyldiimidazole (93 mg, 0.57 mmol) under argon and this solution was stirred for 2 hr at 50° C. Oxetan-3-amine (30 mg, 0.43 mmol) in 3 mL THF was then added and the reaction mixture refluxed for 2 hr. The reaction mixture was then evaporated to dryness in vacuo, dissolved in 10 mL DCM and washed with 2×5 mL of 1 N HCl and 2× with 5 mL of brine. The resulting organic layer was dried with MgSO$_4$, filtered, and concentrated to give the crude intermediate product (196 mg, 86%). The crude product was pure enough by $^1$H NMR to proceed without further purification.

The benzylated intermediate 2-(4-(4-(benzyloxy)-3-isopropylbenzyl)-3,5-dimethylphenoxy)-N-(oxetan-3-yl)acetamide (196 mg, 0.41 mmol) was dissolved in 5 mL of dry methanol with 1 mL THF and 10% Pd/C (100 mg) was added to generate a suspension. The reaction mixture was subjected to vacuum for approximately 1 min, then placed under argon for approximately 1 min. This process was repeated three times to ensure the mixture was properly degassed. Triethylsilane (1 mL, 6.3 mmol) was then added dropwise to the suspension and the reaction mixture was stirred for 4 hrs at room temperature. Filtration over a pad of celite with methanol, concentration in vacuo, and purification via flash chromatography (silica, 10% MeOH in DCM) gave the desired product as a white solid (121 mg, 77% yield). $^1$H NMR (400 MHz, CDCl$_3$): 7.14 (d, J=8.0 Hz, 1H), 6.92 (s, 1H), 6.65 (s, 2H), 6.60 (d, 1H, J=8.2 Hz), 6.54 (dd, 1H, J=8.1, 2.2 Hz), 5.18 (sext. 1H, J=7.6 Hz), 4.97 (t, 2H, J=7.2 Hz), 4.68 (s, OH), 4.57 (t, 2H, J=7.0 Hz), 4.49 (s, 2H), 3.91 (s, 2H), 3.15 (sept., 1H, J=6.9 Hz), 2.23 (s, 6H), 1.21 (d, 6H, J=6.9 Hz).

Example 32—2-(4-(4-hydroxy-3-isopropylbenzyl)-
3,5-dimethylphenoxy)-N-(4-nitrophenyl)acetamide
(Compound 30)

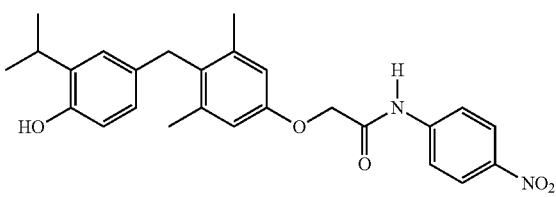 [SMILES: Cc1cc(OCC(=O)Nc2ccc([N+](=O)[O-])cc2)cc(C)c1Cc1ccc(O)c(C(C)C)c1]

A stirring solution of 2-(4-(4-(benzyloxy)-3-isopropylbenzyl)-3,5-dimethylphenoxy)acetic acid (O-benzyl GC1, 150 mg, 0.36 mmol, 1 eq) is treated with dry THF (5 mL) and CDI (140 mg, 0.86 mmol, 2.4 eq) followed by heating to 45° C. for 2 h. The reaction is concentrated under reduced pressure and dissolved into THF (2.5 mL). The reaction solution is treated with 4-nitroaniline (150 mg, 1.075 mmol, 3 eq) and stirred at room temperature for 1 h. The reaction solution is diluted with diethyl ether (20 mL) and washed with 0.5N HCl (2×20 mL) followed by brine (20 mL). The organic layer is dried with Na2SO$_4$ and concentration under reduced pressure. The crude intermediate is purified by flash chromatography (0-40% EtOAc in hexanes) to insure removal of excess 4-nitroaniline. The purified intermediate is taken up in DCM (3 mL) and placed under argon. Pentamethylbenzene (106 mg, 0.72 mmol, 2 eq) is added and the reaction is cooled to −78° C. A solution of BCl$_3$ (1 M DCM, 0.72 mL, 2 eq) is added slowly and the reaction stirs for 15 min. The reaction is quenched with addition of a saturated NaHCO3 solution (2 mL) and the flask is allowed to warm to room temperature. The reaction mixture is diluted with water (10 mL) and extracted with DCM (2×20 mL). The organic layers are combined, dried with Na$_2$SO$_4$, and concentrated under reduced pressure. Purification by flash chromatography (7-60% EtOAc in hexanes) gave the product as a light yellow solid (22 mg, 0.05 mmol, 14%). $^1$H NMR (400 MHz, Chloroform-d) δ 8.30-8.21 (m, 2H), 7.87-7.78 (m, 2H), 6.90 (d, J=2.2 Hz, 1H), 6.71 (s, 2H), 6.66-6.49 (m, 2H), 4.64 (s, 2H), 3.91 (s, 2H), 3.20 (p, J=6.9 Hz, 1H), 2.25 (s, 6H), 1.28-1.16 (m, 6H).

What is claimed is:
1. A compound of Formula II:

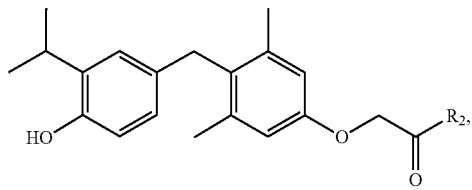

Formula II or a pharmaceutically acceptable salt thereof,
wherein R$_2$ is alkylamino or amino.

2. The compound of claim 1, wherein the compound is of Formula III:

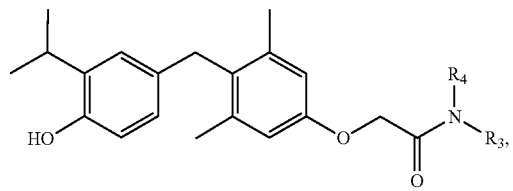

Formula III or a pharmaceutically acceptable salt thereof,
wherein each of R3 and R4 is, independently, H, alkyl, cycloalkyl, substituted alkyl, unsubstituted alkyl, heteroalkyl, saturated alkyl, unsaturated alkyl, aryl, amino, or ethoxy.

3. The compound of claim 2, or a pharmaceutically acceptable salt thereof, wherein R$_3$ is methyl and R$_4$ is methyl.

4. The compound of claim 2, wherein the compound is of Formula IV:

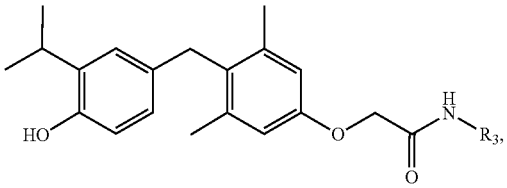

Formula IV or a pharmaceutically acceptable salt thereof,
wherein $R_3$ is H, hydroxyl, amino, methyl, ethyl, propyl, cyclopropyl, 2-hydroxyethyl, 1-hydroxypropan-2-yl, 2-hydroxypropyl, 2-aminoethyl acetate, 2-fluoroethyl, 2,2-difluoroethyl, 2,2,2-trifluoroethyl, phenyl, (4-nitro) phenyl, 2-phenylethyl 2-(2-hydroxyphenyl)ethyl, 2-(3-hydroxyphenyl)ethyl, 2-(3,4-dihydroxyphenyl)ethyl, 3-fluoroethyl; S-methylsulfonyl, 1-(2-hydroxyethyl)-2-hydroxyethyl, 2-propenyl, 2-propynyl, methoxy, 2-ethylsulfonate sodium, cyanomethyl, or oxetanyl.

5. The compound of claim 1, wherein the compound is of Formula III:

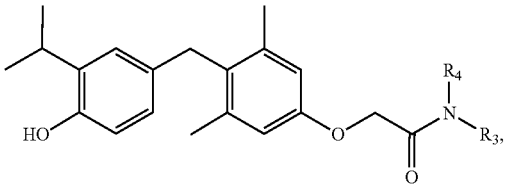

Formula III or a pharmaceutically acceptable salt thereof,
wherein $R_4$ is selected from H and $C_{1-6}$ alkyl; and
$R_3$ is:
(a) H, OH, $NH_2$, $\geq NH(C_{1-6}$ alkyl), $-N(C_{1-6}$ alkyl)$_2$, $-SO_2H$, $-SO_2(C_{1-6}$ alkyl), $C_{2-6}$ alkenyl, $C_{2-6}$ alkynyl, $C_{3-6}$ cycloalkyl, or a 3- to 6-membered heterocyclyl ring containing one heteroatom selected from O, N, and S; or
(b) $C_{1-6}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or
(c) $-O-C_{1-6}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or
(d) a phenyl group optionally substituted by 1, 2, or 3 substituents each independently selected from the group consisting of OH, $NO_2$, and halogen.

6. The compound of claim 5, wherein the compound is of Formula IV:

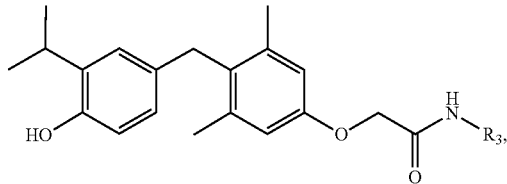

Formula IV or a pharmaceutically acceptable salt thereof,
wherein $R_3$ is:
(a) H, OH, $NH_2$, $-NH(C_{1-6}$ alkyl), $-N(C_{1-6}$ alkyl)$_2$, $-SO_2H$, $-SO_2(C_{1-6}$ alkyl), $C_{2-6}$ alkenyl, $C_{2-6}$ alkynyl, $C_{3-6}$ cycloalkyl, or a 3- to 6-membered heterocyclyl ring containing one heteroatom selected from O, N, and S; or
(b) $C_{1-6}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or
(c) $-O-C_{1-6}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or
(d) a phenyl group optionally substituted by 1, 2, or 3 substituents each independently selected from the group consisting of OH, $NO_2$, and halogen.

7. The compound of claim 5, or a pharmaceutically acceptable salt thereof, wherein $R_3$ is:
(a) H, OH, $NH_2$, $-SO_2H$, $-SO_2(C_{1-3}$ alkyl), $C_{2-3}$ alkenyl, $C_{2-3}$ alkynyl, $C_{3-6}$ cycloalkyl, a 3- to 6-membered heterocyclyl ring containing one heteroatom selected from O, N, and S; or
(b) $C_{1-4}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-3}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or
(c) $-O-C_{1-4}$ alkyl optionally substituted by 1, 2, or 3 substituents each independently selected from OH, halogen, $NH_2$, $-NH(C_{1-6}$ alkyl), $-N(C_{1-6}$ alkyl)$_2$, $-SO_2H$, $-SO_2(C_{1-6}$ alkyl), CN, $C_{3-6}$ cycloalkyl, a 3- to 6-membered heterocyclyl ring containing one heteroatom selected from O, N, and S, or a phenyl group optionally substituted by 1, 2, or 3 substituents each independently selected from the group consisting of OH, $NO_2$, and halogen; or (d) a phenyl group optionally substituted by 1, 2, or 3 substituents each independently selected from the group consisting of OH, NO₂, and halogen.

8. The compound of claim 5, or a pharmaceutically acceptable salt thereof, wherein R₃ is:
(a) H, OH, NH₂, —SO₂H, —SO₂(CH₃), C₂₋₃ alkenyl, C₂₋₃ alkynyl, C₃₋₆ cycloalkyl, a 3- to 6-membered heterocyclyl ring containing one oxygen heteroatom; or
(b) C₁₋₄ alkyl optionally substituted by 1, 2, or 3 substituents each independently selected from OH, F, NH₂, —SO₂H, —SO₂(CH₃), CN, C₃₋₆ cycloalkyl, a 3- to 6-membered heterocyclyl ring containing one oxygen heteroatom, or a phenyl group optionally substituted by 1, 2, or 3 substituents each independently selected from the group consisting of OH, NO₂, and F; or
(c) —O—C₁₋₄ alkyl optionally substituted by 1, 2, or 3 substituents each independently selected from OH, F, NH₂, —SO₂H, —SO₂(CH₃), CN, C₃₋₆ cycloalkyl, a 3- to 6-membered heterocyclyl ring containing one oxygen heteroatom, or a phenyl group optionally substituted by 1, 2, or 3 substituents each independently selected from the group consisting of OH, NO₂, and F; or
(d) a phenyl group optionally substituted by 1, 2, or 3 substituents each independently selected from the group consisting of OH, NO₂, and F.

9. The compound of claim 5, wherein the compound is of Formula IV:

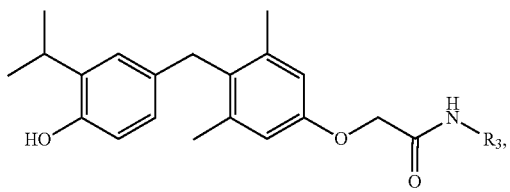

Formula IV or a pharmaceutically acceptable salt thereof,
wherein R₃ is —(CH₂)-phenyl, wherein the phenyl ring is optionally substituted by 1, 2, or 3 substituents each independently selected from the group consisting of OH, NO₂, and F.

10. The compound of claim 5, wherein the compound is of Formula IV:

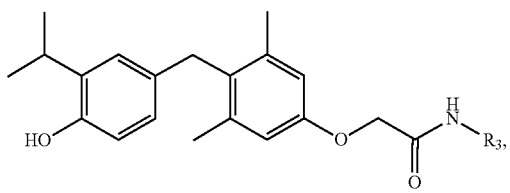

Formula IV or a pharmaceutically acceptable salt thereof,
wherein R₃ is C₁₋₆ alkyl optionally substituted by 1, 2, or 3 substituents each independently selected from the group consisting of OH, F, NH₂, CN, —SO₂H, and —SO₂(C₁₋₆ alkyl).

11. The compound of claim 5, wherein the compound is of Formula IV:

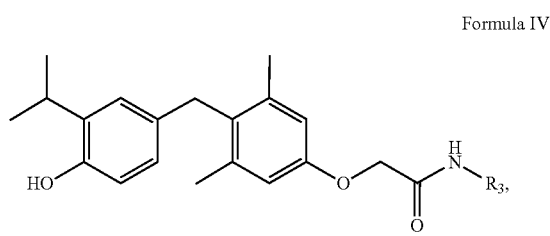

Formula IV or a pharmaceutically acceptable salt thereof,
wherein R₃ is —O—C₁₋₆ alkyl optionally substituted by 1, 2, or 3 F substituents.

12. A compound selected from the group consisting of:

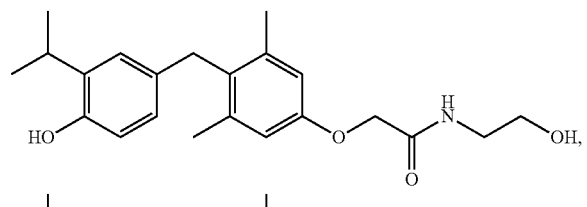

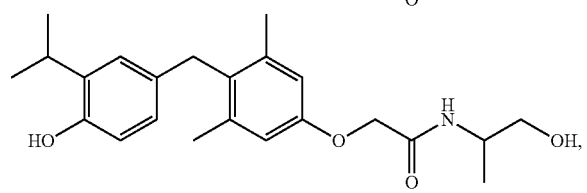

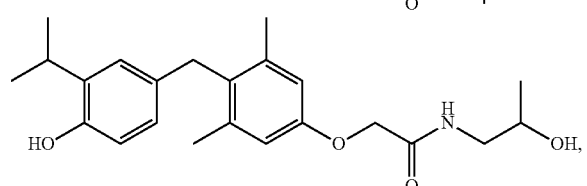

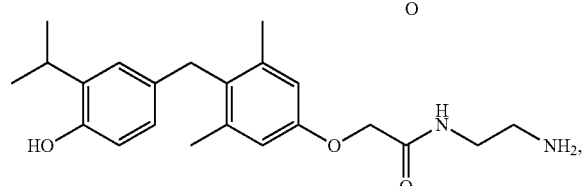

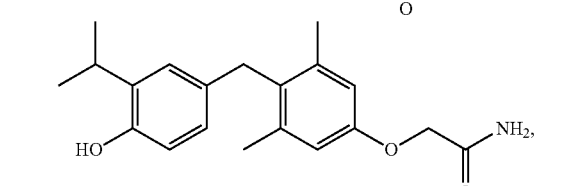

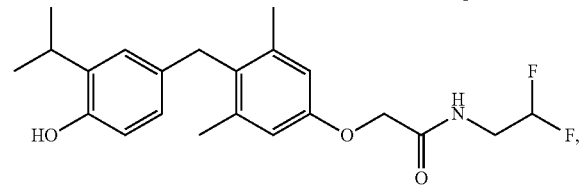

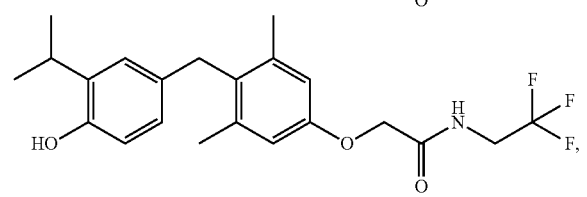

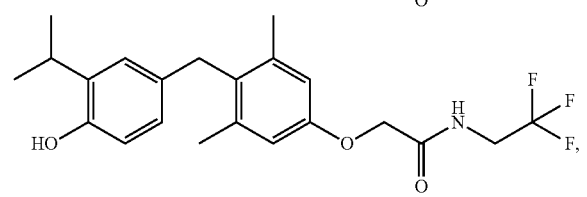

59
-continued
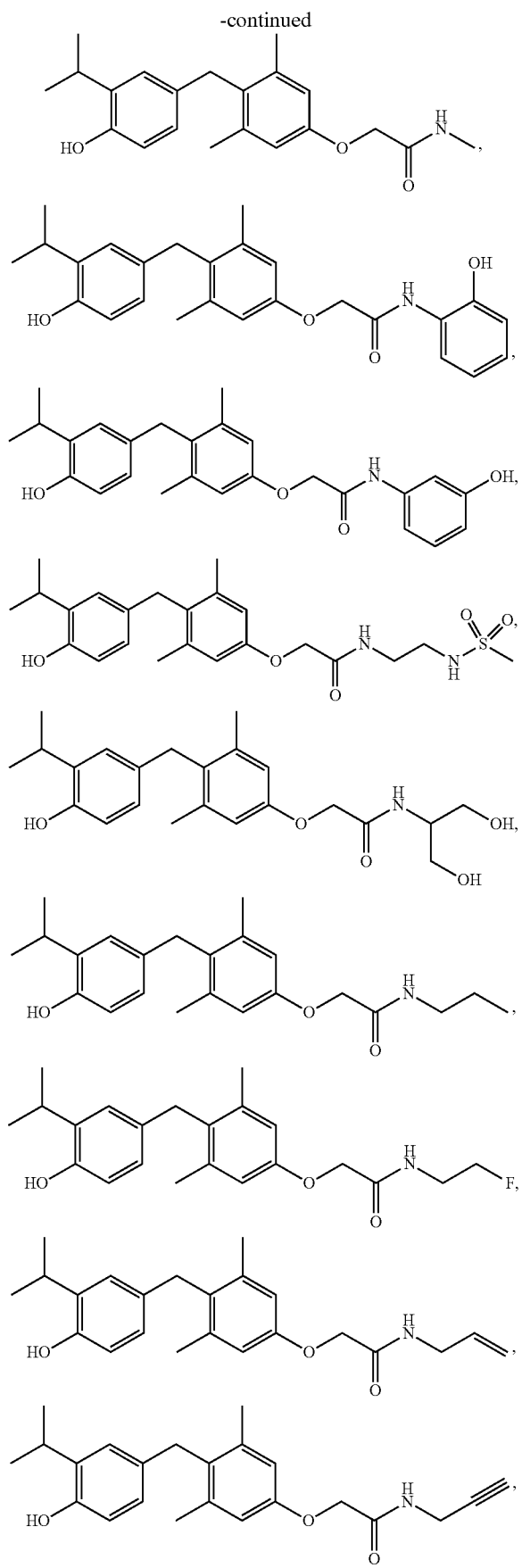
60
-continued
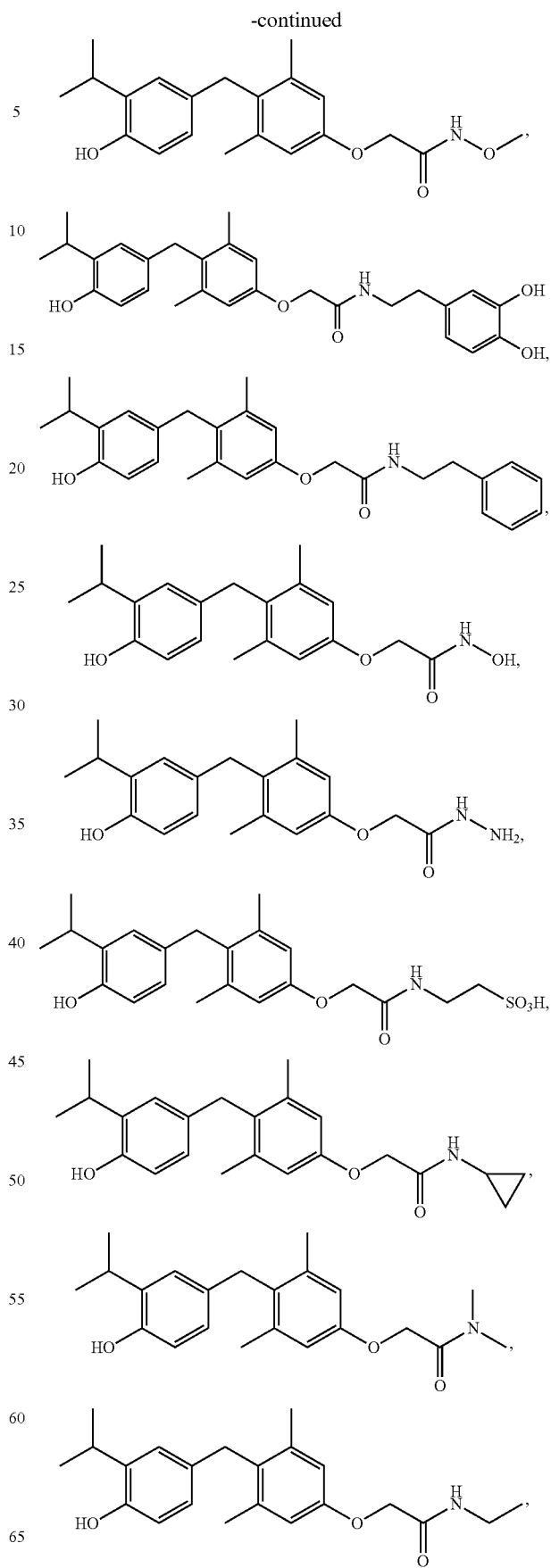

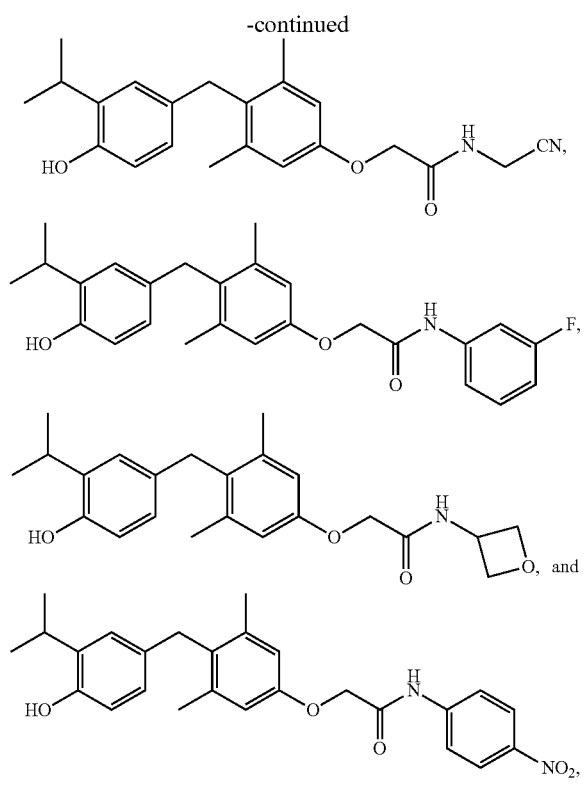

or a pharmaceutically acceptable salt thereof.

13. The compound of claim 1, wherein the compound is selected from the group consisting of:
- 2-(4-(4-hydroxy-3-isopropylbenzyl)-3,5-dimethylphenoxy)-N-(2-hydroxyethyl)acetamide;
- 2-(4-(4-hydroxy-3-isopropylbenzyl)-3,5-dimethylphenoxy)-N-(1-hydroxypropan-2-yl)acetamide;
- 2-(4-(4-hydroxy-3-isopropylbenzyl)-3,5-dimethylphenoxy)-N-(2-hydroxypropyl)acetamide;
- 2-(2-(4-(4-hydroxy-3-isopropylbenzyl)-3,5-dimethylphenoxy)acetamido)ethan-1-aminium acetate;
- 2-(4-(4-hydroxy-3-isopropylbenzyl)-3,5-dimethylphenoxy)acetamide;
- N-(2,2-difluoroethyl)-2-(4-(4-hydroxy-3-isopropylbenzyl)-3,5-dimethylphenoxy)acetamide;
- 2-(4-(4-hydroxy-3-isopropylbenzyl)-3,5-dimethylphenoxy)-N-(2,2,2-trifluoroethyl)acetamide;
- 2-(4-(4-hydroxy-3-isopropylbenzyl)-3,5-dimethylphenoxy) -N-methylacetamide;
- 2-(4-(4-hydroxy-3-isopropyl benzyl)-3, 5-dimethylphenoxyl)-N-(2-hydroxyphenyl) acetamide;
- 2-(4-(4-hydroxy-3-isopropyl benzyl)-N-(3-hydroxyphenyl) acetamide;
- 2-(4-(4-hydroxy-3-isopropylbenzyl)-3,5-dimethylphenoxy)-N-(2-(methyl sulfonamido)ethyl)acetamide;
- N-(1,3-dihydroxypropan-2-yl)-2-(4-(4-hydroxy-3-isopropylbenzyl)-3,5-dimethylphenoxy)acetamide 2-(4-(4-hydroxy-3-isopropylbenzyl)-3, 5-dimethylphenoxy)-N-propylacetamide;
- N-(2-fluoroethyl)-2-(4-(4-hydroxy-3-isopropylbenzyl)-3,5-dimethylphenoxy)acetamide;
- N-allyl-2-(4-(4-hydroxy-3-isopropylbenzyl)-3,5-dimethylphenoxy)acetamide;
- 2-(4-(4-hydroxy-3-isopropylbenzyl)-3,5-dimethylphenoxy)-N-(prop-2-yn-1-yl)acetamide;
- 2-(4-(4-hydroxy-3-isopropylbenzyl)-3,5-dimethylphenoxy)-N -methoxyacetamide;
- N-(3,4-dihydroxyphenethyl)-2-(4-(4-hydroxy-3-isopropylbenzyl)-3,5- dimethylphenoxy)acetamide;
- 2-(4-(4-hydroxy-3-isopropylbenzyl)-3,5-dimethylphenoxy)-N -phenethylacetamide;
- N-hydroxy-2-(4-(4-hydroxy-3-isopropylbenzyl)-3,5-dimethylphenoxy)acetamide;
- 2-(4-(4-hydroxy-3-isopropylbenzyl)-3,5-dimethylphenoxy)acetohydrazide;
- 2-(2-(4-(4-hydroxy-3-isopropylbenzyl)-3,5-dimethylphenoxy)acetamido)ethane-1-sulfonate N-cyclopropyl-2-(4-(4-hydroxy-3-isopropylbenzyl)-3,5-dimethylphenoxy)acetamide;
- 2-(4-(4-hydroxy-3-isopropylbenzyl)-3,5-dimethylphenoxy)-N,N -dimethylacetamide;
- N-ethyl-2-(4-(4-hydroxy-3-isopropylbenzyl)-3,5-dimethylphenoxy)acetamide;
- N-(cyanomethyl)-2-(4-(4-hydroxy-3-isopropylbenzyl)-3, 5-dimethylphenoxy)acetamide;
- N-(3-fluorophenyl)-2-(4-(4-hydroxy-3-isopropylbenzyl)-3,5-dimethylphenoxy)acetamide;
- 2-(4-(4-hydroxy-3-isopropylbenzyl)-3,5-dimethylphenoxy)-N-(oxetan-3-yl)acetamide; and
- 2-(4-(4-hydroxy-3-isopropylbenzyl)-3,5-dimethylphenoxy)-N-(4-nitrophenyl)acetamide, or a pharmaceutically acceptable salt thereof.

14. A pharmaceutical composition comprising a pharmaceutically effective amount of the compound of claim 1, or a pharmaceutically acceptable salt thereof, and one or more pharmaceutically acceptable carriers.

* * * * *